(12) United States Patent
Tan et al.

(10) Patent No.: US 11,167,268 B2
(45) Date of Patent: Nov. 9, 2021

(54) CATALYST AND METHOD FOR MANUFACTURING THE SAME AND METHOD FOR HYDROGENATING AROMATIC EPOXY COMPOUND

(71) Applicant: National Tsing Hua University, Hsinchu (TW)

(72) Inventors: Chung-Sung Tan, Hsinchu (TW); Wei-Yuan Lu, Kaohsiung (TW)

(73) Assignee: National Tsing Hua University, Hsinchu (TW)

( * ) Notice: Subject to any disclaimer, the term of this patent is extended or adjusted under 35 U.S.C. 154(b) by 186 days.

(21) Appl. No.: 16/663,894

(22) Filed: Oct. 25, 2019

(65) Prior Publication Data

US 2021/0086167 A1  Mar. 25, 2021

(30) Foreign Application Priority Data

Sep. 25, 2019  (TW) ................ 108134704

(51) Int. Cl.
*B01J 23/656* (2006.01)
*B01J 23/42* (2006.01)
(Continued)

(52) U.S. Cl.
CPC ........... *B01J 23/6567* (2013.01); *B01J 21/18* (2013.01); *B01J 23/42* (2013.01); *B01J 35/10* (2013.01); *B01J 37/04* (2013.01); *C07C 29/158* (2013.01)

(58) Field of Classification Search
CPC . B01J 21/18; B01J 23/42; B01J 23/464; B01J 35/10; B01J 35/1014; B01J 35/1019;
(Continued)

(56) References Cited

U.S. PATENT DOCUMENTS 3,383,406 A * 5/1968 Achard .................. C07C 69/15
560/243
3,978,000 A * 8/1976 Schmitt, Jr. ............. B01J 21/18
502/185
(Continued)

FOREIGN PATENT DOCUMENTS

| DE | 10 2018 215394 | * | 3/2020 | ........... C07C 29/145 |
| JP | 2002-338559 | * | 11/2002 | ............. C07B 61/00 |
| JP | 2002-338560 | * | 11/2002 | ............... B01J 23/46 |

OTHER PUBLICATIONS

Kundu et al., "Rhodium metal-rhodium oxide (Rh—Rh2O3) nanostructures with Pt-like or better activity towards hydrogen evolution and oxidation reactions (HER, HOR) in acid and base: correlating its HOR/HER activity with hydrogen binding energy and oxophilicity of the catalyst", Journal of Materials Chemistry A, Oct. 25, 2018, pp. 23531-23541, vol. 6.

(Continued)

*Primary Examiner* — Patricia L. Hailey
(74) *Attorney, Agent, or Firm* — The Webb Law Firm

(57) ABSTRACT

A catalyst includes a carbon black support and active metal particles. A surface of the carbon black support has a relative atomic percentage of oxygen atoms ranged from 2 atom % to 12 atom %. The active metal particles are distributed on the carbon black support. Each of the active metal particles includes rhodium metal and rhodium oxide. A method for manufacturing the catalyst and a method for hydrogenating an aromatic epoxy compound are also provided herein.

19 Claims, 14 Drawing Sheets

(51) Int. Cl.
*B01J 35/10* (2006.01)
*B01J 37/04* (2006.01)
*C07C 29/158* (2006.01)
*B01J 21/18* (2006.01)

(58) Field of Classification Search
CPC ........ B01J 35/1035; B01J 37/04; B01J 37/34; B01J 37/346; C07C 29/158
USPC ............. 502/5, 185, 326; 523/400; 562/400; 423/449.1, 449.3, 449.5; 528/421
See application file for complete search history.

(56) References Cited

U.S. PATENT DOCUMENTS

| | | | |
|---|---|---|---|
| 7,108,939 B2 * | 9/2006 | Suzuki | H01M 4/926 |
| | | | 429/532 |
| 10,537,882 B2 * | 1/2020 | Shi | C01B 32/15 |
| 2002/0077504 A1 * | 6/2002 | Albers | B01J 23/464 |
| | | | 564/423 |
| 2003/0098649 A1 * | 5/2003 | Murai | C08G 59/1405 |
| | | | 313/512 |
| 2006/0194063 A1 * | 8/2006 | Murai | C08G 59/1405 |
| | | | 428/413 |
| 2010/0028059 A1 * | 2/2010 | Wu | G03G 15/162 |
| | | | 399/302 |
| 2020/0173045 A1 * | 6/2020 | Chen | C02F 1/722 |

OTHER PUBLICATIONS

Xu et al., "Microwave-assisted synthesis of mutually embedded Rh concave nanocubes with enhanced electrocatalytic activity", RSC Advances, Jun. 18, 2019, pp. 19126-19130, vol. 9.

Yang et al., "Enhanced Electrokinetics of C—C Bond Splitting during Ethanol Oxidation by using a Pt/Rh/Sn Catalyst with a Partially Oxidized Pt and Rh Core and a SnO2 Shell", ChemCatChem, Sep. 4, 2016, pp. 2876-2880, vol. 8.

Lu et al., "Hydrogenation of Bisphenol A-Type Epoxy Resin (BE186) over Vulcan XC72-Supported Rh and Rh—Pt Catalysts in Ethyl Acetate-Containing Water", Industrial & Engineering Chemistry Research, 2019, pp. 16326-16337, vol. 58.

* cited by examiner

CATALYST AND METHOD FOR MANUFACTURING THE SAME AND METHOD FOR HYDROGENATING AROMATIC EPOXY COMPOUND

CROSS-REFERENCE TO RELATED APPLICATION

This application claims priority to Taiwanese Patent Application No. 108134704 filed Sep. 25, 2019, the disclosure of which is hereby incorporated by reference in its entirety.

BACKGROUND

Field of Invention

The present disclosure relates to a catalyst for hydrogenating an aromatic epoxy compound and a method for manufacturing the same, and a method for hydrogenating an aromatic epoxy compound.

Description of Related Art

Light-emitting diodes (LEDs) have a share of 38% in the entire lighting market. As the advances in white-light LED technologies, the requirements for the packaging material have become stricter. Since the spectrum of light emitted from the white-light LED includes short-wavelength light, the packaging material of LED is prone to be deteriorated, as referred to as "yellowing" of the material, which causes the decrease in luminous brightness.

Conventionally, the packaging material of LED is bisphenol A (BPA) epoxy resin, which has a severe issue of "yellowing" caused by heat. In a long term thermal aging test, the transmittances of short-wavelength light decrease due to the yellowing of the material, and a phenomenon of "color shift" occurs.

General solutions to prevent the "yellowing" of material include adding an anti-UV agent to epoxy resin, using polysiloxane resin as the packaging material, and using hydrogenated epoxy resin as the packaging material. The addition of anti-UV agent and the usage of the polysiloxane resin are relatively mature technologies, but still have disadvantages such as poor optical properties of the materials, complicated processes, and high cost. In contrast, the hydrogenated epoxy resin, especially hydrogenated bisphenol A epoxy resin, possesses good resistance to the "yellowing" because the epoxy groups thereof show good symmetry in structure, and has ether groups.

However, it is difficult to manufacture the hydrogenated epoxy resin since the epoxy groups of the epoxy resin are also hydrogenated when the epoxy resin is hydrogenated. Therefore, there is an urgent need to develop better techniques for hydrogenating the epoxy resin.

SUMMARY

One aspect of the present disclosure provides a catalyst, which includes a carbon black support and active metal particles. A surface of the carbon black support has a relative atomic percentage of oxygen atoms ranging from 2 atom % to 12 atom %. The active metal particles are distributed on the carbon black support. The active metal particles include rhodium metal and rhodium oxide.

In some embodiments, the carbon black support has a specific surface area (BET) of less than 200 m$^2$/g.

In some embodiments, the carbon black support has a pore volume of less than 0.5 cm$^3$/g.

In some embodiments, each of the active metal particles further includes platinum metal.

In some embodiments, in the active metal particles, the number of rhodium atoms in the rhodium oxide is 45-60% of the total number of rhodium atoms.

In some embodiments, rhodium of the rhodium oxide includes $Rh^{3+}$ and $Rh^{1+}$.

In some embodiments, a ratio of the number of rhodium atoms of the rhodium oxide to the number of rhodium atoms of the rhodium metal ranges from 1 to 1.5.

Another aspect of the present disclosure provides a method for manufacturing a catalyst, which includes: (i) providing a reaction precursor including an alcohol reducing agent, a rhodium precursor, and a carbon black support; (ii) mixing the reaction precursor with an alkali to obtain an alkaline precursor; (iii) irradiating the alkaline precursor with microwaves to reduce the rhodium precursor in the alkaline precursor to an active metal containing rhodium metal and rhodium oxide; and (iv) mixing the alkaline precursor irradiated by the microwaves with an acid such that the active metal containing the rhodium metal and the rhodium oxide is adsorbed on the carbon black support to form the catalyst.

In some embodiments, irradiating the alkaline precursor with the microwaves includes: reducing 40-55 atom % of rhodium atoms in the rhodium precursor to the rhodium metal and reducing 45-60 atom % of rhodium atoms in the rhodium precursor to the rhodium oxide.

In some embodiments, the carbon black support has a pore volume of less than 0.5 cm$^3$/g.

In some embodiments, the carbon black support has a specific surface area of less than 200 m$^2$/g.

In some embodiments, the rhodium precursor includes (i) rhodium chloride hydrate or (ii) rhodium chloride hydrate and chloroplatinic acid hexahydrate, in which mixing the reaction precursor with the alkali includes: forming an ion having a chemical formula of $Rh(OH)_6^{3-}$.

In some embodiments, mixing the reaction precursor with the alkali includes: adjusting a pH value of the alkaline precursor to 10-13.

In some embodiments, mixing the alkaline precursor irradiated by the microwaves with the acid includes: adjusting a pH value of the alkaline precursor to 1-4.

Another aspect of the present disclosure provides a method for hydrogenating an aromatic epoxy compound, which includes: (i) providing the catalyst described above; and (ii) hydrogenating a solution containing an aromatic epoxy compound and a solvent using the catalyst, in which the solvent includes ethyl acetate.

In some embodiments, the solvent further includes water, and a weight percentage of the water in the solvent is 1 to 5 wt %.

In some embodiments, in the hydrogenating operation, a weight ratio of the aromatic epoxy compound to the catalyst ranges from (2-5):0.05.

In some embodiments, the aromatic epoxy compound includes bisphenol A epoxy resin or bisphenol A diglycidyl ether.

In some embodiments, the hydrogenating operation is performed in an environment at a temperature ranging from 30° C. to 80° C.

DETAILED DESCRIPTION

Figure 1:
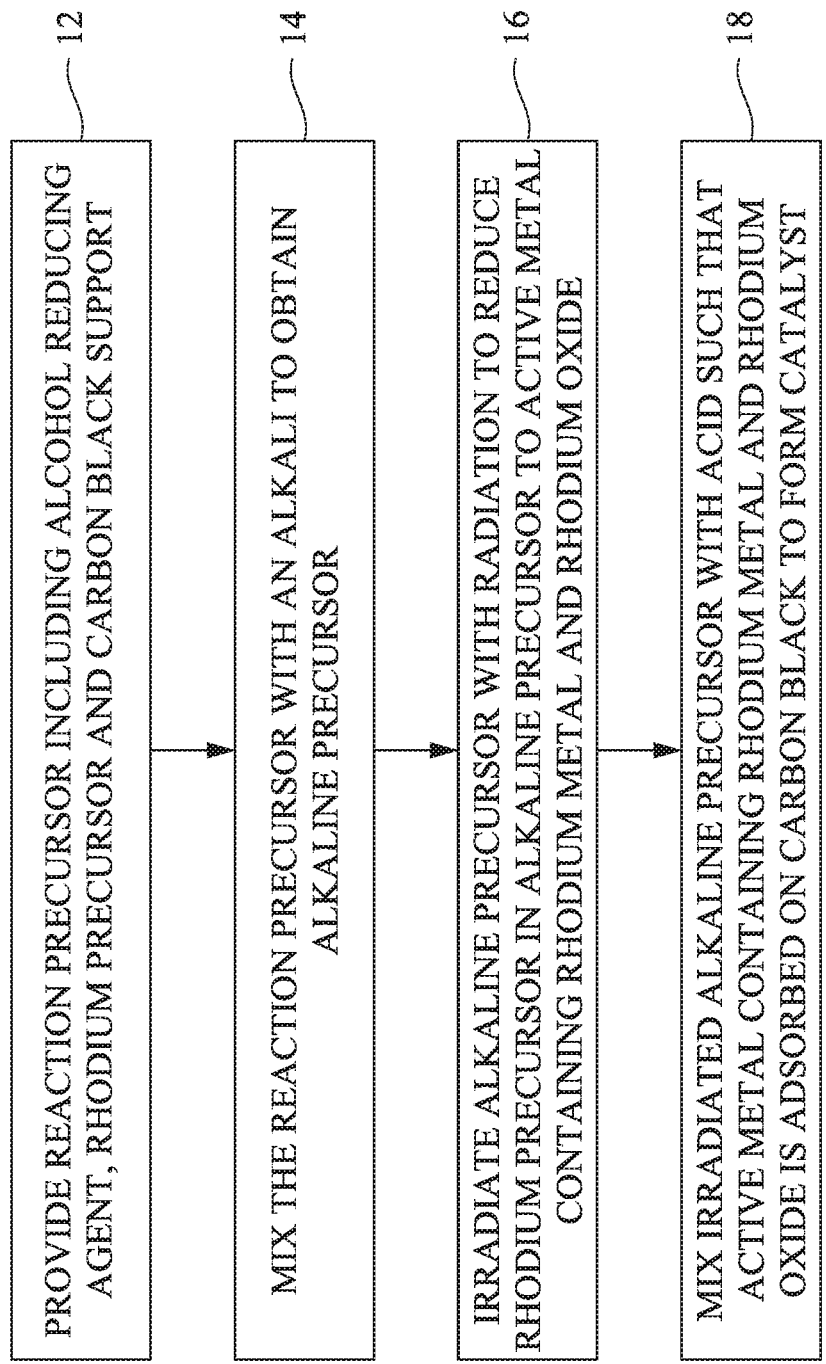
FIG. 1 is a flow chart of a method for manufacturing a catalyst according to various embodiments of the present disclosure.

In order to make the description of the present disclosure more detailed and complete, the illustrative description of aspects and specific embodiments of the present disclosure is set forth below; however, this is not the only form in which the specific embodiments of the present disclosure are implemented or utilized. The embodiments disclosed herein may be combined or substituted with each other in an advantageous manner, and other embodiments may be added to an embodiment without further description.

In the following description, numerous specific details will be described in detail to enable the reader to fully understand the following embodiments. However, the embodiments of the present disclosure may be practiced without these specific details. In other instances, well-known structures and devices are only schematically shown in the drawings to simplify the drawings.

In order to make the description of the present disclosure more detailed and complete, the illustrative description of aspects and specific embodiments of the present disclosure is set forth below; however, this is not the only form in which the specific embodiments of the present disclosure are implemented or utilized. The embodiments disclosed herein may be combined or substituted with each other in an advantageous manner, and other embodiments may be added to an embodiment without further description.

In the following description, numerous specific details will be described in detail to enable the reader to fully understand the following embodiments. However, the embodiments of the present disclosure may be practiced without these specific details. In other instances, well-known structures and devices are only schematically shown in the drawings to simplify the drawings.

One aspect of the present disclosure is to provide a method of manufacturing a catalyst. FIG. 1 is a flow chart illustrating a method 10 for manufacturing a catalyst according to various embodiments of the present disclosure. The method includes operation 12, operation 14, operation 16 and operation 18.

In operation 12, a reaction precursor is provided, and the reaction precursor includes an alcohol reducing agent, a rhodium precursor, and a carbon black support. In some embodiments, the rhodium precursor includes rhodium chloride hydrate (chemical formula: $RhCl_3.xH_2O$, Rh content: 38.5-45.5 wt %), or the like. In yet some embodiments, the rhodium precursor includes rhodium chloride hydrate and chloroplatinic acid hexahydrate (chemical formula: $H_2PtCl_6.6H_2O$).

In some embodiments, the carbon black support has a pore volume of less than 0.5 $cm^3/g$, such as 0.45 $cm^3/g$, 0.4 $cm^3/g$, 0.30 $cm^3/g$, 0.20 $cm^3/g$, 0.17 $cm^3/g$, 0.10 $cm^3/g$ or 0.05 $cm^3/g$, but not limited thereto. In some embodiments, the carbon black support has a specific surface area of less than 200 $m^2/g$, such as 190 $m^2/g$, 180 $m^2/g$, 170 $m^2/g$, 160 $m^2/g$, 150 $m^2/g$, 140 $m^2/g$, 130 $m^2/g$, 120 $m^2/g$, 110 $m^2/g$ or 100 $m^2/g$. Please note that the use of the carbon black as the support provides special technical effects, which will be described in more detail below.

In some embodiments, the alcohol reducing agent includes a polyol reducing agent (e.g., ethylene glycol). In one embodiment, the alcohol reducing agent includes ethylene glycol and water, and a volume ratio of ethylene glycol to water ranges from 10:1 to 1:1 (ethylene glycol:water), such as 8:1, 7:1, 6:1, 5:1, 4:1, 3:1, 2:1 or 1:1.

In operation 14, the reaction precursor is mixed with an alkali to obtain an alkaline precursor. In some embodiments, after mixing the reaction precursor with the alkali, the rhodium precursor (e.g., rhodium chloride hydrate) forms an ion having a chemical formula of $Rh(OH)_6^{3-}$. The alkaline precursor obtained by mixing the reaction precursor with the alkali has a pH value of 10-13, such as 10, 10.5, 11, 11.5, 12, 12.5, or 13. After the reaction precursor is mixed with the alkali, as the hydroxyl group ($OH^-$) provided by the alkali is a relatively stronger ligand as compared with the reaction precursor, hydroxyl groups substitute for the ligands of the rhodium precursor so to form $Rh(OH)_6^{3-}$, and the alkaline precursor is more stable. In one embodiment, the alkali may be an aqueous solution of sodium hydroxide.

In operation 16, the alkaline precursor is irradiated with radiation to reduce the rhodium precursor in the alkaline precursor to an active metal containing rhodium metal and rhodium oxide. Specifically, the alkaline precursor is irradiated using radiation, such as microwaves. The molecules may be oscillated by the microwaves to generate heat, and therefore the polyol reducing agent can effectively convert the microwaves into heat to promote the reduction reaction. In some embodiments, in the reduction reaction described above, 40-55 atom % (e.g., 40 atom %, 45 atom %, 50 atom % or 55 atom %) of rhodium in the rhodium precursor is reduced and converted into the rhodium metal, and 45-60 atom % (e.g., 60 atom %, 55 atom %, 50 atom % or 45 atom %) of rhodium in the rhodium precursor is reduced and converted into the rhodium oxide. It is noted that the reducing ability of the alcohol reducing agent used herein is relatively weak, so that it needs to be heated to enhance the reducing ability thereof. Furthermore, the aforementioned alkaline precursor has hydroxyl ligands, which are not easily to be reduced completely, so that the active metal contains rhodium oxide which is incompletely reduced. In the case where the pH value is adjusted to the range of 10-13, most of the alcohol reducing agent is present in the form of a salt after the reduction reaction is performed. It is noted that the active metal containing both the rhodium metal and the rhodium oxide provides certain technical effects, which will be described in more detail hereinafter.

Similarly, in the embodiments that the rhodium precursor includes rhodium chloride hydrate and chloroplatinic acid hexahydrate, the rhodium precursor is reduced and converted into rhodium metal, platinum metal and rhodium oxide in the reduction reaction. Herein, 40-55 atom % of rhodium in the rhodium precursor is reduced to the rhodium metal, and 45-60 atom % of rhodium in the rhodium precursor is reduced to the rhodium oxide.

In operation 18, the irradiated alkaline precursor is mixed with an acid such that the active metal containing rhodium metal and rhodium oxide is adsorbed onto the carbon black support, thereby obtaining catalyst. Specifically, the irradiated alkaline precursor is mixed with the acid such that the pH value of the alkaline precursor is adjusted to the range of 1-4. After the pH value of the alkaline precursor is adjusted to 1-4 by mixing the alkaline precursor with the acid, coordination ability of the acid salt with respect to the active metal is decreased, which facilitates the adsorption of the active metal on the carbon support. In one embodiment, the acid may be an aqueous solution containing hydrochloric acid.

Another aspect of the present disclosure is to provide a catalyst. The catalyst can be used to hydrogenate an aromatic epoxy compound. The catalyst includes a carbon black support and a plurality of active metal particles. In various embodiments, the active metal particles are distributed on the carbon black support. The active metal particles include rhodium metal (Rh(0)) and rhodium oxide ($RhO_x$, x is a value ranged from 1 to 3), and thus the composition of the active metal particles can be represented as $RhO_x$—Rh(0). In various embodiments, rhodium of the rhodium oxide includes $Rh^{+3}$ and $Rh^{+1}$, in which a molar number of $Rh^{+3}$ is greater than that of $Rh^{+1}$. In one embodiment, the active metal particles further include platinum metal ($Pt^0$). For example, the active metal particles include rhodium metal ($Rh^0$), rhodium oxide ($RhO_x$) and platinum metal ($Pt^0$), and the composition of the active metal particles can be represented as $RhO_x$—Rh(0)-Pt(0).

In some embodiments, among the active metal particles, the amount of rhodium atoms in the rhodium oxide is 45-60% (for example 45%, 47%, 49%, 51%, 53%, 55%, 57%, 59%, and 60%) of the total amount of rhodium atoms. In other embodiments, a ratio of the amount of the rhodium atoms of the rhodium oxide to that of the rhodium metal, i.e. (the rhodium atoms of the rhodium oxide)/(the rhodium atoms of the rhodium metal), is in a range of from 1 to 1.5, such as 1.05, 1.1, 1.12, 1.14, 1.16, 1.18, 1.2, 1.3, 1.4 and 1.5. According to some embodiments of the present disclosure, the synergistic action of the rhodium oxide and the rhodium metal allows the catalyst to have satisfactory hydrogenation ability and less side reactions. When the number of the rhodium atoms of the rhodium oxide relative to the total rhodium atoms is too high or too low, the hydrogenation ability of the catalyst may be lowered or more side reactions may be generated.

In some embodiments, the active metal particles have an average particle size ranging from about 1.5 nm to about 5 nm, for example about 1.5 nm, about 2.1 nm, about 2.6 nm, about 3.1 nm, about 3.6 nm, and about 4.1 nm, but the present disclosure is not limited thereto.

The relative atomic percentage of oxygen atoms on the surface of the carbon black support ranges from 2 atom % to 12 atom %, for example 2 atom %, 4 atom %, 6 atom %, 8 atom %, 10 atom % and 12 atom %. The Method for measuring the relative atomic percentage of the oxygen atoms on the surface of the carbon black support may be X-ray photoelectron spectroscopy. In the present disclosure, the relative atomic percentage of the oxygen atoms on the surface of the carbon black support is defined by the following Formula (1):

(the number of the oxygen atoms on the surface of the carbon black support/the total number of atoms on the surface of the carbon black support)×100%  Formula (1).

According to various embodiments of the present disclosure, if the relative atomic percentage of the oxygen atoms on the surface of the carbon black support surface is less than 2 atom %, the active metal particles may not be anchored by the carbon black support, resulting in leaching of the active metal particles. To the contrary, if the relative atomic percentage of the oxygen atoms on the surface of the carbon black support is greater than 12 atom %, a side reaction such as a ring-opening reaction of epoxy groups occurs. In various embodiments, the carbon black support is a carbon black support of Vulcan® XC series, for example Vulcan® XC72, Vulcan® XC72R, Vulcan® XC200 and Vulcan® XC500.

In other embodiments, the carbon black support has an average particle size ranging from about 25 μm to about 60 μm, such as 25 μm, 30 μm, 40 μm, 50 μm, 54 μm, 55 μm and 60 μm, but the present disclosure is not limited thereto.

In some embodiments, the carbon black support has a specific surface area (BET) of less than 200 m²/g, for example 190 m²/g, 180 m²/g, 170 m²/g, 160 m²/g, 150 m²/g, 140 m²/g, 130 m²/g, 120 m²/g, 110 m²/g, 100 m²/g, 90 m²/g, 80 m²/g and 70 m²/g.

In yet some embodiments, the carbon black support has a pore volume of less than 0.5 cm³/g, for example 0.45 cm³/g, 0.4 cm³/g, 0.30 cm³/g, 0.20 cm³/g, 0.10 cm³/g or 0.05 cm³/g. According to some embodiments of the present disclosure, the specific surface area and pore volume properties of the carbon black support provide certain technical effects, which will be described in more detail hereinafter.

Figure 2:
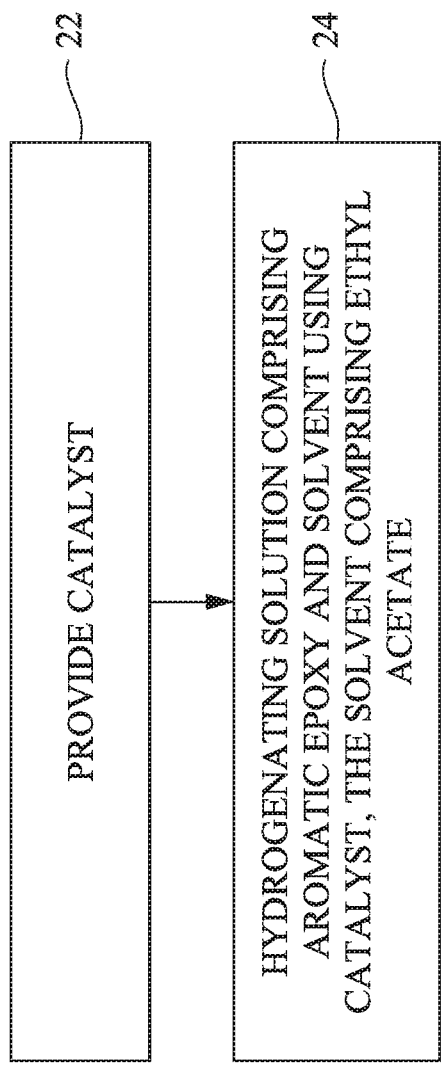
FIG. 2 is a flow chart of a method for hydrogenating an aromatic epoxy compound according to various embodiments of the present disclosure.

Another aspect of the present disclosure provides a method for hydrogenating an aromatic epoxy compound. FIG. 2 is a flow chart illustrating a method 20 for hydrogenating an aromatic epoxy compound according to various embodiments of the present disclosure. The method 20 includes operation 22 and operation 24. In operation 22, the catalyst of any embodiment described above is provided. The embodiments of the preparation of the catalyst are described hereinbefore, and are not repeatedly described herein.

In operation 24, a solution containing an aromatic epoxy compound and a solvent is hydrogenated using the catalyst, in which the solvent includes ethyl acetate. According to various embodiments, ethyl acetate can provide a better hydrogenation yield as compared to other solvents. In some embodiments, the solvent includes ethyl acetate and water, and a weight percentage of the water in the solvent is 1 to 5%, such as 1%, 2%, 3%, 4%, or 5%. Water can form a hydrogen bond with the epoxy group of the aromatic epoxy compound, which greatly increases the hydrogenation reactivity of the benzene ring in the aromatic epoxy compound. The solvent used in the embodiments of the present disclosure is a green solvent which is environmentally friendly, as compared to other highly toxic organic solvents. The solvent not only is environmentally friendly but also considerably enhances the hydrogenation reactivity.

In some embodiments, illustrative examples of the aromatic epoxy compound include bisphenol A diglycidyl ether and bisphenol A epoxy resin. In various examples, the aromatic epoxy compound has an epoxy equivalent ranged from 150 g/eq to 2000 g/eq, for example 186 g/eq, 751 g/eq and 1772 g/eq.

In some embodiments, in the hydrogenation reaction, a weight ratio of the aromatic epoxy compound to the catalyst is in a range of (2-5):0.05 (aromatic epoxy compound: catalyst), for example 2:0.05, 2.5:0.05, 3:0.05, 4:0.05, and 5:0.05. According to various embodiments, if the above weight ratio is greater than a certain value (e.g., 5), the reaction rate of the hydrogenation reaction is too low. On the other hand, if the above weight ratio is less than a certain value (e.g., 2), a ratio of the epoxy ring opening is increased to an unacceptable level. Therefore, according to some embodiments, there is a preferred range of the weight ratio of the aromatic epoxy compound to the catalyst.

In some embodiments, the hydrogenation reaction is performed in an environment at a temperature ranging from 30° C. to 80° C., for example 30° C., 40° C., 50° C., 60° C., 70° C. and 80° C. According to various embodiments, when the hydrogenation temperature is too high (e.g., high than 80° C.), the ratio of epoxy ring opening is unfavorably increased. In contrast, when the hydrogenation temperature is too low (e.g., less than 40° C.), the reaction rate of the hydrogenation reaction is too slow. Therefore, according to some embodiments, there is a preferred temperature range.

After the hydrogenation reaction is carried out, a catalyst using carbon black as the carbon support (e.g., $Rh_5$/carbon black) exhibits a relatively greater yield of hydrogenation. Specifically, as compared to a commercial catalyst ($Rh_5$/C) and catalysts prepared from other carbon supports (e.g., activated carbon and mesoporous carbon), the catalyst prepared from the carbon black support, according to the embodiments of the present disclosure, provides a higher yield of hydrogenation. According to various embodiments, since the specific surface area and the pore volume of the carbon black support are within the ranges described hereinbefore, during the hydrogenation reaction, bisphenol A epoxy resin is not detained in the pores for a time period too long, and consequently the occurrence of the side reactions can be reduced, thereby providing excellent yield of hydrogenation.

In addition, the hydrogenation yield of the catalyst prepared by the present disclosure is much higher than that of a catalyst prepared using wet impregnation or chemical fluid deposition. Specifically, the catalyst prepared using the wet impregnation and the catalyst prepared using the chemical fluid deposition does not contain rhodium oxide but only contain rhodium metal ($Rh^0$), so that the hydrogenation yield is low. It is confirmed that the rhodium oxide is an extremely important promoter for hydrogenation in the hydrogenation reaction.

In addition, the reaction rate of hydrogenation using a monometallic catalyst (composed of $RhO_x$—Rh(0)) is lower than that using a bimetallic catalyst (composed of $RhO_x$—Rh(0)-Pt(0)), but the monometallic catalyst exhibits a lower ratio of epoxy ring opening. Although the bimetallic catalyst exhibits a faster reaction rate, the ratio of epoxy ring opening is considerably higher than that of the monometallic catalyst.

The following embodiments are presented to illustrate the specific aspects of the present disclosure, and the present disclosure may be practiced by those of one skilled in the art. However, the following embodiments should not be used to limit the present disclosure.

(A) Solvent Selection

In Examples 1-13, a commercial catalyst $Rh_5$/C (purchased from Sigma Aldrich Co., Ltd.) was used to hydrogenating bisphenol A epoxy resin in different solvents to determine preferable solvents. The hydrogenation reaction of bisphenol A epoxy resin (DGEBA, a molecular weight of 373 g/mol, hereinafter referred to BE186, supplied by Chang Chun Plastics Co., Ltd.) was carried out in a semi-batch system. The experimental method is briefly described below. First, 2 g BE186, different kinds of solvents, and 0.05 g $Rh_5$/C (commercial catalyst, purchased from Sigma Aldrich Co., Ltd.) were mixed and then added into a high pressure autoclave equipped with a glass vessel and a cross rod magnetic stirrer (Parr). Subsequently, hydrogen gas in a pressure of 1,000 psi was then charged into the reactor after several hydrogen purges, and hydrogenation reaction was performed at 40° C. for 2 hours. After the reaction was completed, the reactor was depressurized and cooled down to ambient temperature, and reaction products were collected. Subsequently, the reaction products were centrifuged to remove catalyst traces, and the solvent was removed by rotary evaporation at 40° C. to 80° C. to obtain purified products. Detailed experimental conditions are summarized in Table 1 below.

Viscosity (cps) of the reaction mixture and hydrogenation yield (%) and specific activity ($h^{-1}$) of the purified products are listed in Table 1. The hydrogenation yields of all Examples in the present disclosure were calculated from the cyclohexane signals (after hydrogenation of BE186) and the benzene ring signals (before hydrogenation of BE186) measured by $^1$H-NMR (purchased from Bruker Co., Ltd., AVANCE-500) at a frequency of 500 MHz. The specific activity was defined as: (molar number of hydrogenated bisphenol type epoxy resin)/(molar number of Rh)×$h^{-1}$.

TABLE 1

Hydrogenation of bisphenol A epoxy resin using commercial catalyst ($Rh_5$/C) (solvent effect)

| Example No. | BE186 Weight (g) | Catalyst | Catalyst Weight (g) | Solvent | Solvent Weight (g) | Concentration (wt%) | Viscosity (cps) | Time (h) | Hydrogenation yield (%) | Specific activity ($h^{-1}$) |
|---|---|---|---|---|---|---|---|---|---|---|
| 1 | 2 | $Rh_5$/C | 0.05 | None | None | 100 | 11620 | 2 | 6.6 | 7.1 |
| 2 | 2 | $Rh_5$/C | 0.05 | $H_2O$ | 2 | 50 | 11620 | 2 | 23.7 | 25.5 |

TABLE 1-continued

Hydrogenation of bisphenol A epoxy resin using commercial catalyst (Rh$_5$/C) (solvent effect)

| Example No. | BE186 Weight (g) | Catalyst | Catalyst Weight (g) | Solvent | Solvent Weight (g) | Concentration (wt%) | Viscosity (cps) | Time (h) | Hydrogenation yield (%) | Specific activity (h$^{-1}$) |
|---|---|---|---|---|---|---|---|---|---|---|
| 3 | 2 | Rh$_5$/C | 0.05 | THF | 2 | 50 | 4.09 | 2 | 59.6 | 64.2 |
| 4 | 2 | Rh$_5$/C | 0.05 | EA | 2 | 50 | 3.71 | 2 | 65.7 | 70.8 |
| 6 | 2 | Rh$_5$/C | 0.05 | Solvent A | 2 | 50 | 4.05 | 2 | 65.4 | 70.5 |
| 7 | 2 | Rh$_5$/C | 0.05 | Solvent B | 2 | 50 | 3.53 | 2 | 70.4 | 75.8 |
| 8 | 2 | Rh$_5$/C | 0.05 | Solvent C | 2 | 50 | 3.52 | 2 | 71.7 | 77.3 |
| 9 | 2 | Rh$_5$/C | 0.05 | Solvent D | 2 | 50 | 3.40 | 2 | 57.7 | 62.2 |
| 10 | 2 | Rh$_5$/C | 0.05 | Solvent E | 2 | 50 | 3.24 | 2 | 49.2 | 53.0 |
| 11 | 2 | Rh$_5$/C | 0.05 | Solvent F | 2 | 50 | 3.15 | 2 | 46.8 | 50.4 |
| 12 | 2 | Rh$_5$/C | 0.05 | Solvent G | 2 | 50 | 3.76 | 2 | 77.8 | 83.8 |
| 13 | 2 | Rh$_5$/C | 0.05 | Solvent H | 2 | 50 | 3.32 | 2 | 56.0 | 60.3 |

Remarks:
Solvent A was 94 wt % of tetrahydrofuran (THF, HPLC grade reagent) and 6 wt % of water (H$_2$O)
Solvent B was 90 wt % of THF and 10 wt % of methanol (MeOH, HPLC grade reagent)
Solvent C was 80 wt % of THF and 20 wt % of MeOH
Solvent D was 70 wt % of THF and 30 wt % of MeOH
Solvent E was 60 wt % of THF and 40 wt % of MeOH
Solvent F was 50 wt % of THF and 50 wt % of MeOH
Solvent G was 97 wt % of ethyl acetate (EA, HPLC grade reagent) and 3 wt % of H$_2$O
Solvent H was 80 wt % of EA and 20 wt % of MeOH
Catalyst type: represented in the form of Mx/carbon support, M = metal species, and x = the theoretical wt % loading of the metal In Example 1 of Table 1, it was found that the viscosity of the reaction mixture without using a solvent was as high as 11,620, and thus hydrogenation reaction failed to be effectively performed on BE186, so that the solvent played an important role in the hydrogenation reaction.

It could be observed in Example 2 that solubility of BE186 in water was poor, and the viscosity of the reaction mixture was also as high as 11,620. Specifically, when water was used as the solvent, hydrogen bonding was formed between water and the epoxy group of the epoxy resin, and thus the reactivity of the benzene ring of the epoxy resin in hydrogenation was greatly improved. However, water could also be used as a relatively weaker nucleophile. When BE186 was dispersed in water for hydrogenation, the epoxy group of BE186 might suffer the risk of ring-opening. In another aspect, the solubility of BE186 in water was very low, resulting in a decrease in the hydrogenation yield. In addition, from Example 3 and Example 4, the hydrogenation yield using ethyl acetate (EA) as a solvent was better than that using tetrahydrofuran (THF) as a solvent.

Examples 7-11 were carried out by mixing THF and MeOH in different ratios as the solvents. From the results of Examples 7-11, it was found that when the amount of MeOH was gradually increased from 10 wt % to 50 wt %, the hydrogenation yield increased to a maximum value and then gradually decreased. The hydrogenation yield of Example 8 was the highest in Examples 7-11. From this result, it could be inferred that since MeOH was also adsorbed on the surface of the catalyst, and the adsorption of the epoxy resin was competed with MeOH when too much MeOH was present, resulting in a decrease in the hydrogenation yield. It was noted that the hydrogenation yield of Example 12 was as high as 77.8%, and the solvent G (3 wt % H$_2$O+97 wt % EA) had relatively higher hydrogenation yield.

(B) Catalyst Preparation

Monometallic catalysts and bimetallic catalysts were prepared using a modified microwave assisted polyol reduction method. Specifically, 0.2 g of different kinds of carbon supports (activated carbon, mesoporous carbon, and carbon black) and metal precursor (RhCl$_3$.xH$_2$O (Rh content: 38.5 wt % to 45.5 wt %, purchased from Alfa-Aesar Co., Ltd.) and/or H$_2$PtCl$_6$.6H$_2$O (Pt content: 37.5 wt %, purchased from Alfa-Aesar Co., Ltd.)) were dissolved into 120 ml of a mixed solvent composed of ethylene glycol (EG, purity: 99%, purchased from Alfa-Aesar Co., Ltd.) and water, and a volume ratio of ethylene glycol to water was 3:1 (v/v). Next, the pH value was adjusted to 11-12 using 1N aqueous sodium hydroxide solution (analytical grade reagent) followed by ultra-sonication for 90 minutes to obtain a catalyst slurry. The precursor and the carbon support in the catalyst slurry were uniformly distributed in the solvent. After the ultra-sonication treatment, the catalyst slurry was heated using a household microwave oven two times (900 W, 30 seconds each time). After the catalyst slurry was cooled down to ambient temperature, the pH value was adjusted to 2-3 using 1N aqueous hydrochloric acid solution (analytical grade reagent) to precipitate metal nanoparticles onto the surface of the carbon support to obtain a crude catalyst product. Finally, the catalyst was collected by suction filtration, and then washed by abundant water and dried overnight in an oven at 80° C.

In Examples described below, the catalysts prepared by the wet impregnation method and chemical fluid deposition (CFD) method were also studied.

(C) Catalyst Analysis

Figure 3:
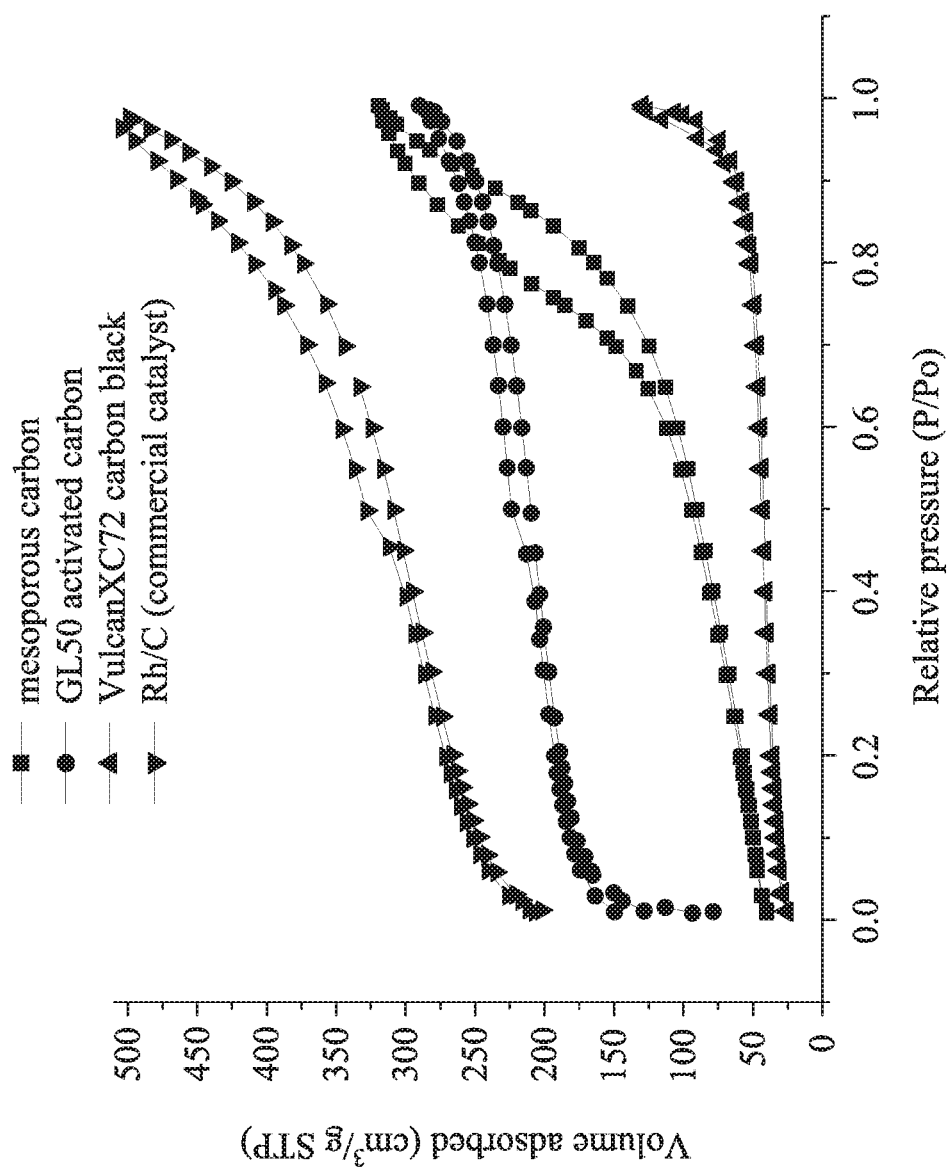
FIG. 3 is a graph showing nitrogen isothermal adsorption/desorption curves of a commercial catalyst and various carbon supports.

FIG. 3 is a graph showing nitrogen isothermal adsorption/desorption curves of a commercial catalyst and various carbon supports. The specific surface area (S$_{BET}$) of carbon support/catalyst, pore diameter (d$_p$), and total pore volume (V$_p$) could be calculated from the isothermal adsorption/desorption curve, in which Barret-Joyner-Halenda (BJH) method was used for calculating the pore diameter and the total pore volume. The specific surface areas, pore diameters, and total pore volumes of the commercial catalyst (Example 14) and various carbon supports (Examples 15-17) are summarized in Table 2 below.

The average particle sizes and particle size distributions (PSD) of the active metal particles in the commercial catalyst and the prepared catalysts were analyzed using TEM images, and the results are also summarized in Table 2. Examples 18-20 and 23 of Table 2 were catalysts prepared using the modified microwave assisted polyol reduction method, in which Examples 18 to 20 were the monometallic catalysts, and Example 23 was the bimetallic catalyst ($Rh_{2.5}Pt_{2.5}$/carbon black). Further, Example 21 ($Rh_5$/carbon black-imp) was the catalyst prepared by the wet impregnation method, and Example 22 ($Rh_5$/carbon black-CFD) was the catalyst prepared by the chemical fluid deposition method.

TABLE 2

Physical properties and particle size analysis of carbon support/catalyst

| Example | Carbon support/catalyst | $S_{BET}$ (m²/g) | $d_p$ (nm) | $V_P$ (cm³/g) | PSD (nm) |
|---|---|---|---|---|---|
| 14 | $Rh_5$/C(commercial catalyst) | 853.8 | 3.8 | 0.52 | 2.9 ± 1.5 |
| 15 | Activated carbon | 604.5 | 3.7 | 0.23 | |
| 16 | Mesoporous carbon | 205.2 | 10.0 | 0.50 | |
| 17 | Carbon black | 116.4 | N.A | 0.17 | |
| 18 | $Rh_5$/activated carbon | | | | 3.3 ± 1.4 |
| 19 | $Rh_5$/mesoporous carbon | | | | 2.5 ± 0.7 |
| 20 | $Rh_5$/carbon black | | | | 3.1 ± 1.2 |
| 21 | $Rh_5$/carbon black-imp | | | | 5.5 ± 2.1 |
| 22 | $Rh_5$/carbon black-CFD | | | | 4.0 ± 1.4 |
| 23 | $Rh_{2.5}P_{t2.5}$/carbon black | | | | 3.1 ± 1.0 |

Figure 4:
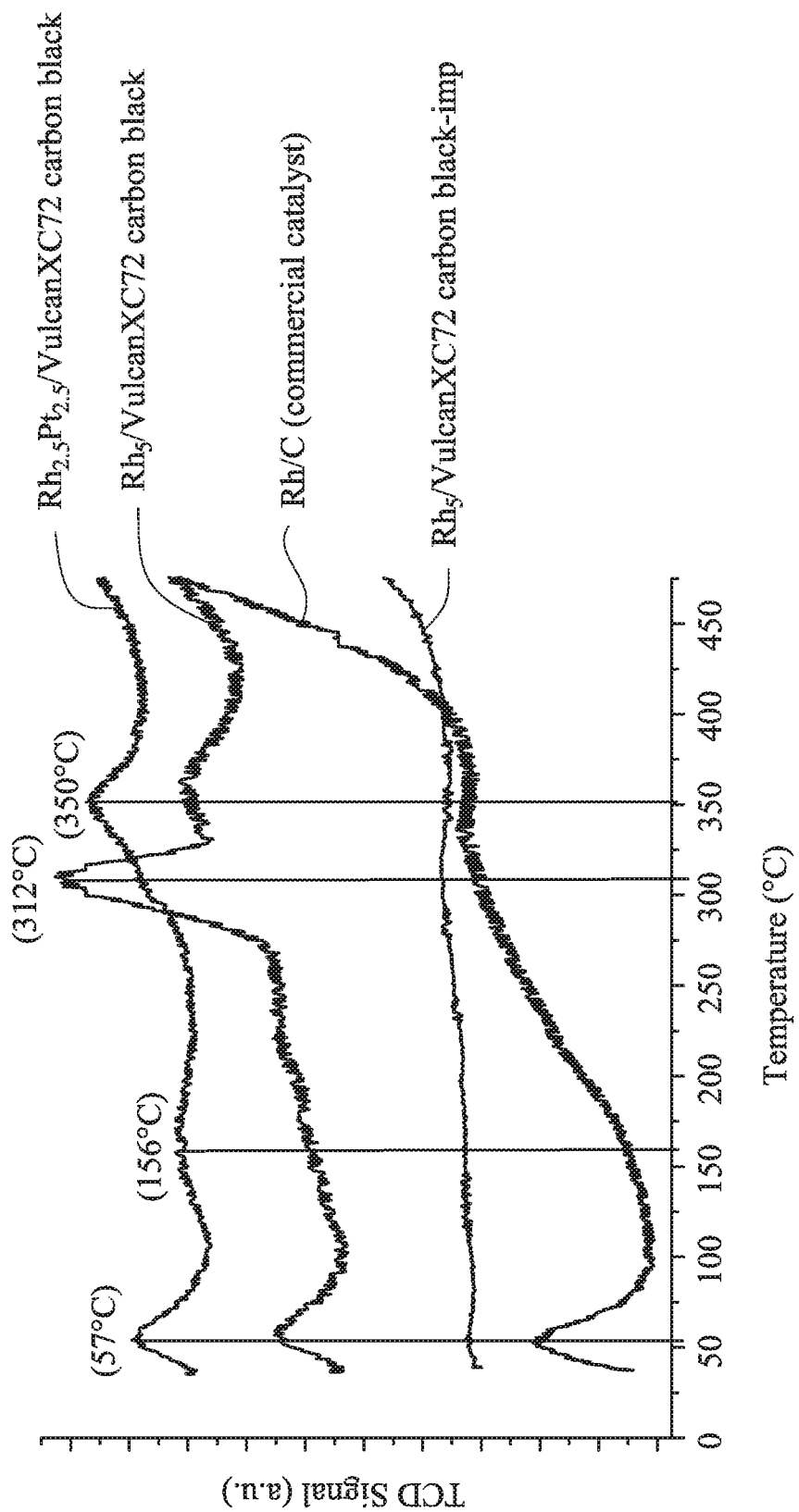
FIG. 4 is a graph showing measurement results of temperature-programmed reduction ($H_2$-TPR) of the commercial catalyst and the catalysts prepared in Embodiments 20, 21 and 23.

Remarks:
Carbon support/catalyst: represented in the form of Mx/carbon support, M is metal species, and x is the theoretical wt % loading of the metal
Rh5/C: commercial catalyst, Model No. MFCD00011, purchased from Sigma Aldrich Co., Ltd.
Activated Carbon: Model No. Norit GL 50, purchased from Cabot Co., Ltd.
Mesoporous carbon: Model No. 633100, purchased from Sigma Co., Ltd.
Carbon black: Vulcan ® XC72, purchased from Cabot Co., Ltd.
N.A: non available FIG. 4 is a graph showing measurement results of temperature-programmed reduction ($H_2$-TPR) of the commercial catalyst and the catalysts prepared in Examples 20, 21 and 23. As shown in FIG. 2, hydrogen consumption was observed (<400° C.). However, degradation of the carbon material must occur above 500° C. According to this result, it could be speculated the presence of oxides in the catalyst.

Figure 5:
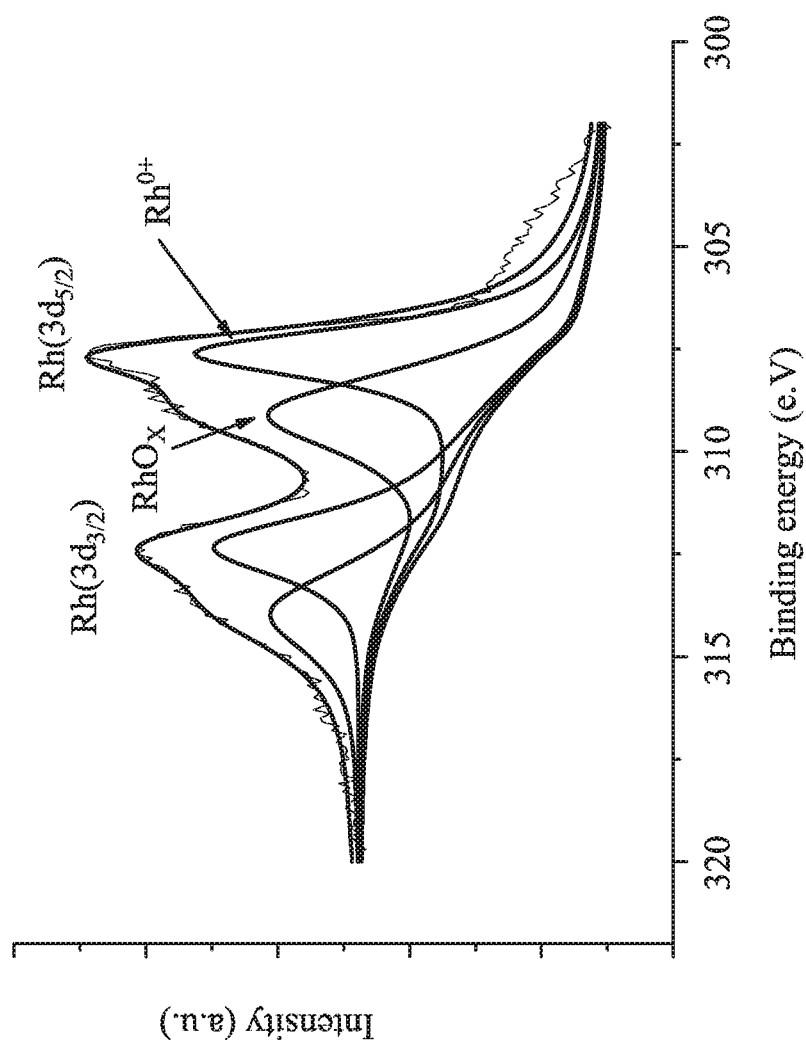
FIG. 5 is a graph showing measurement results of X-ray photoelectron spectroscopy (XPS) peak fitting (Rh 3d) of the commercial catalyst $Rh_5$/C of Embodiment 14.
Figure 6:
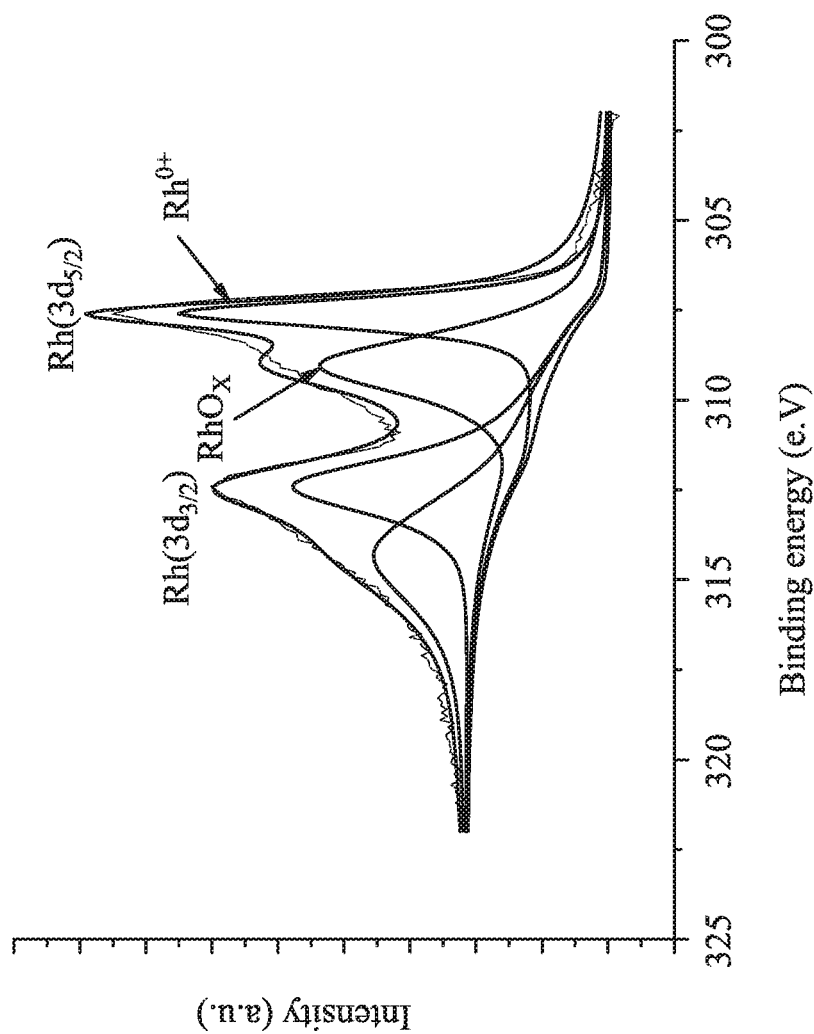
FIG. 6 is a graph showing measurement results of XPS peak fitting (Rh 3d) of the catalyst $Rh_5$/activated carbon of Embodiment 18.
Figure 7:
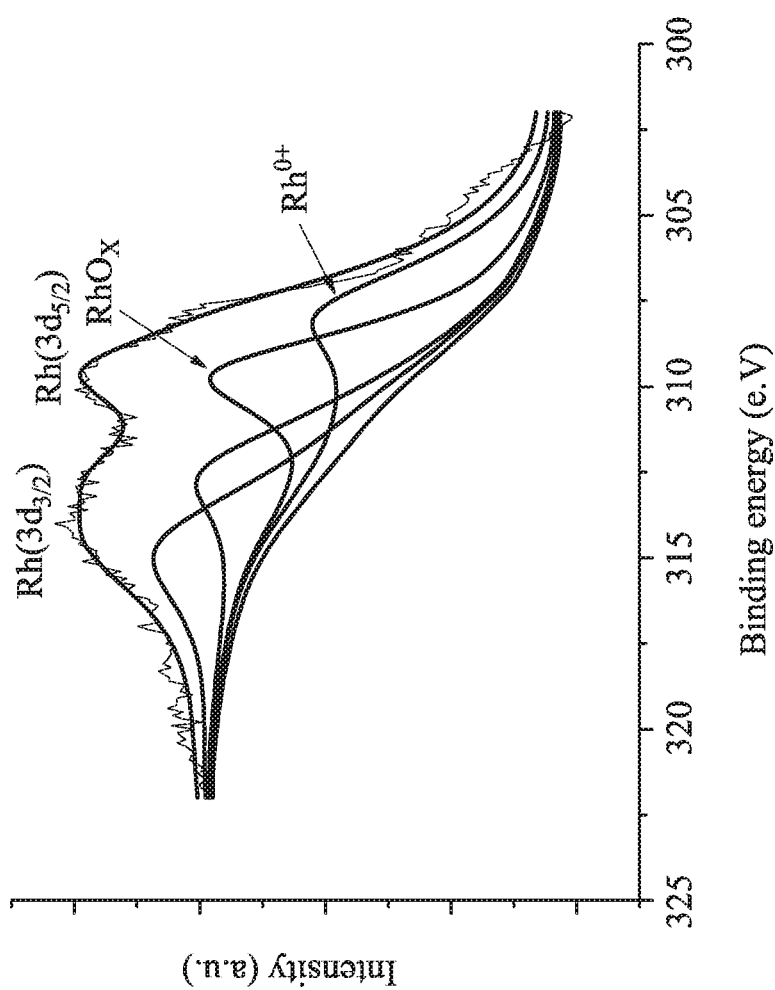
FIG. 7 is a graph showing measurement results of XPS peak fitting (Rh 3d) of the catalyst $Rh_5$/mesoporous carbon of Embodiment 19.
Figure 8:
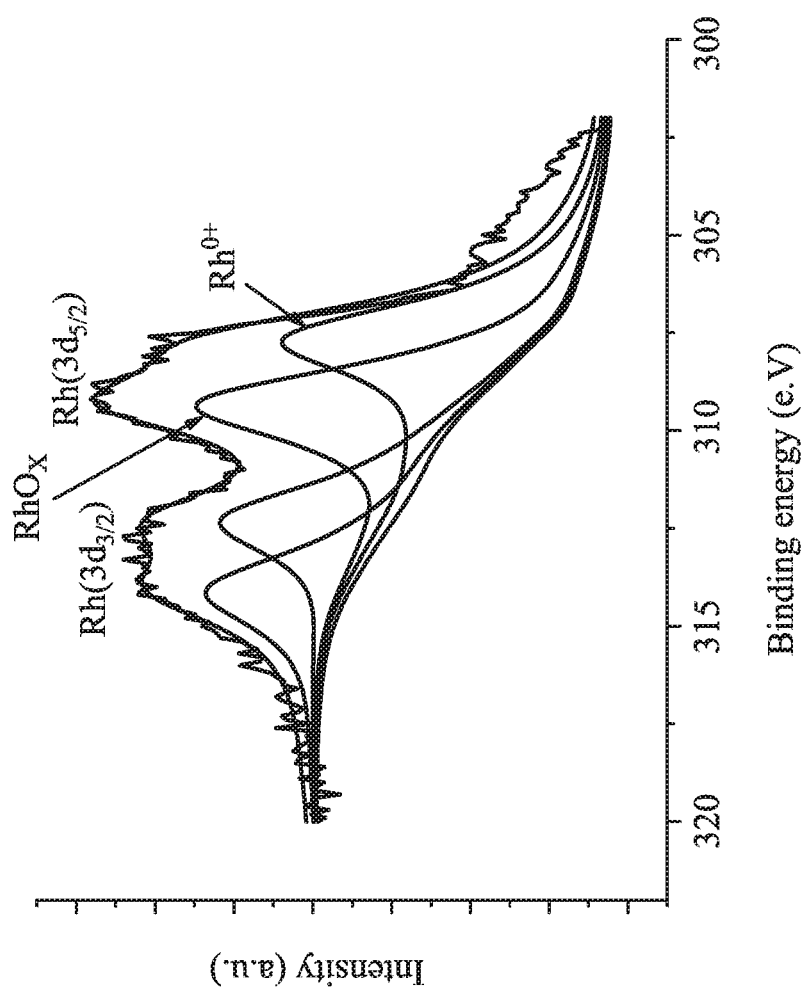
FIG. 8 is a graph showing measurement results of XPS peak fitting (Rh 3d) of the catalyst $Rh_5$/carbon black of Embodiment 20.
Figure 9:
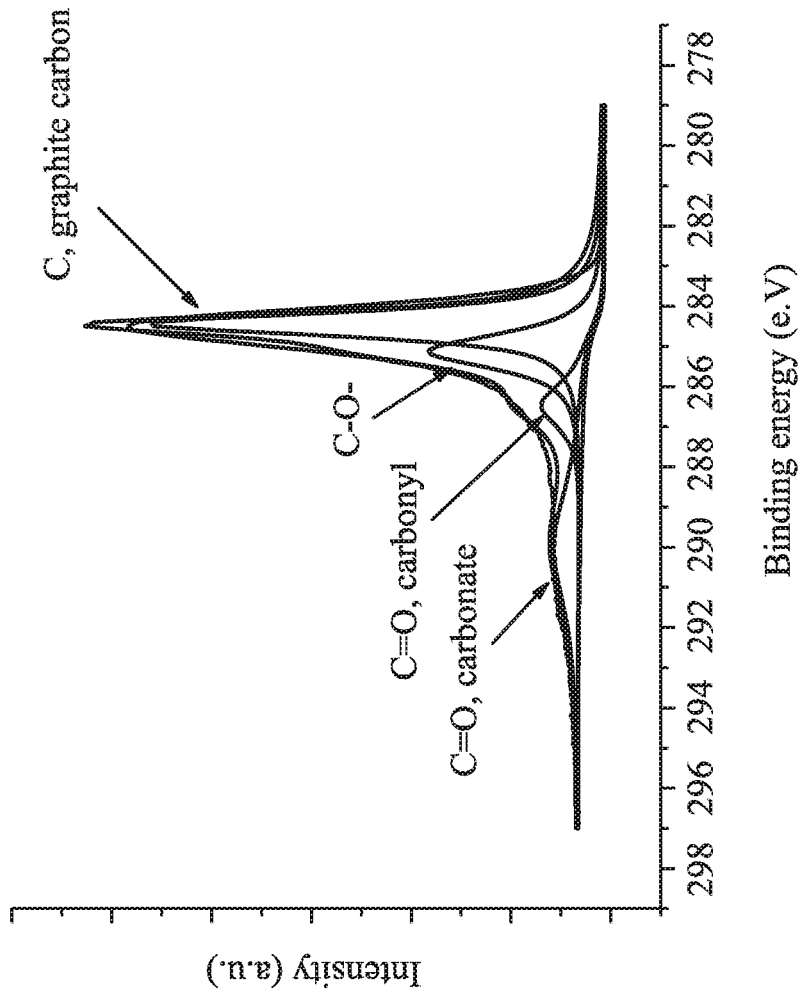
FIG. 9 is a graph showing measurement results of XPS peak fitting (C 2s) of the catalyst $Rh_5$/carbon black of Embodiment 20.
Figure 10:
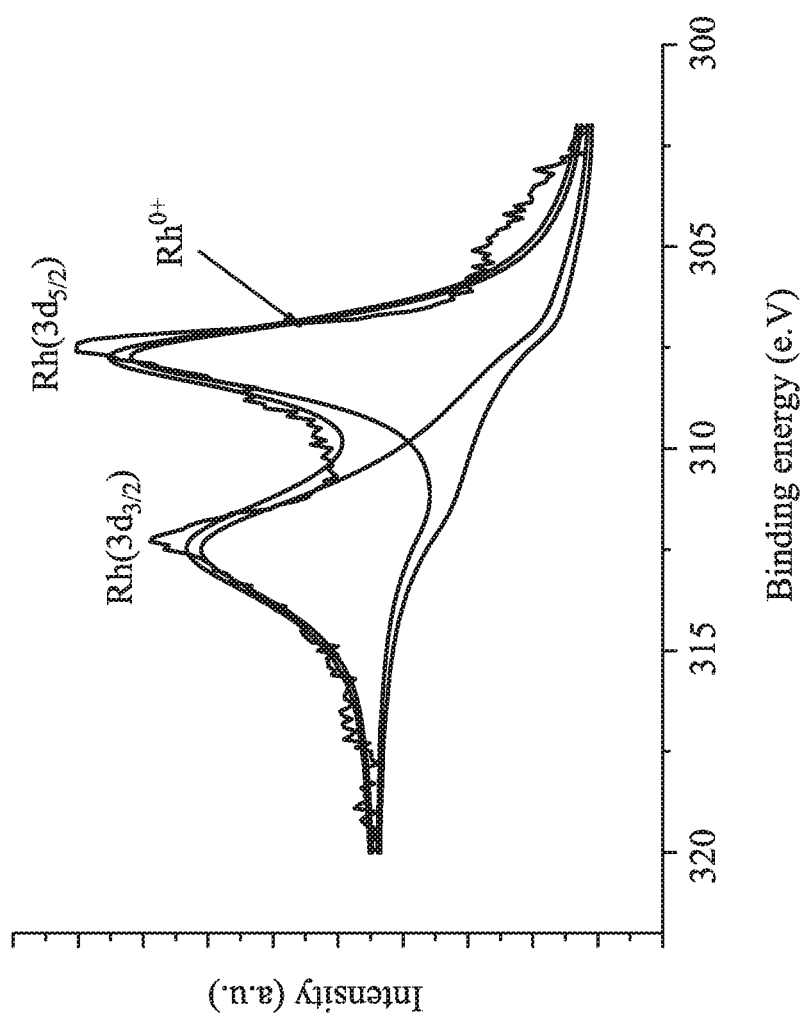
FIG. 10 is a graph showing measurement results of XPS peak fitting (Rh 3d) of the catalyst $Rh_5$/carbon black-imp of Embodiment 21.
Figure 11:
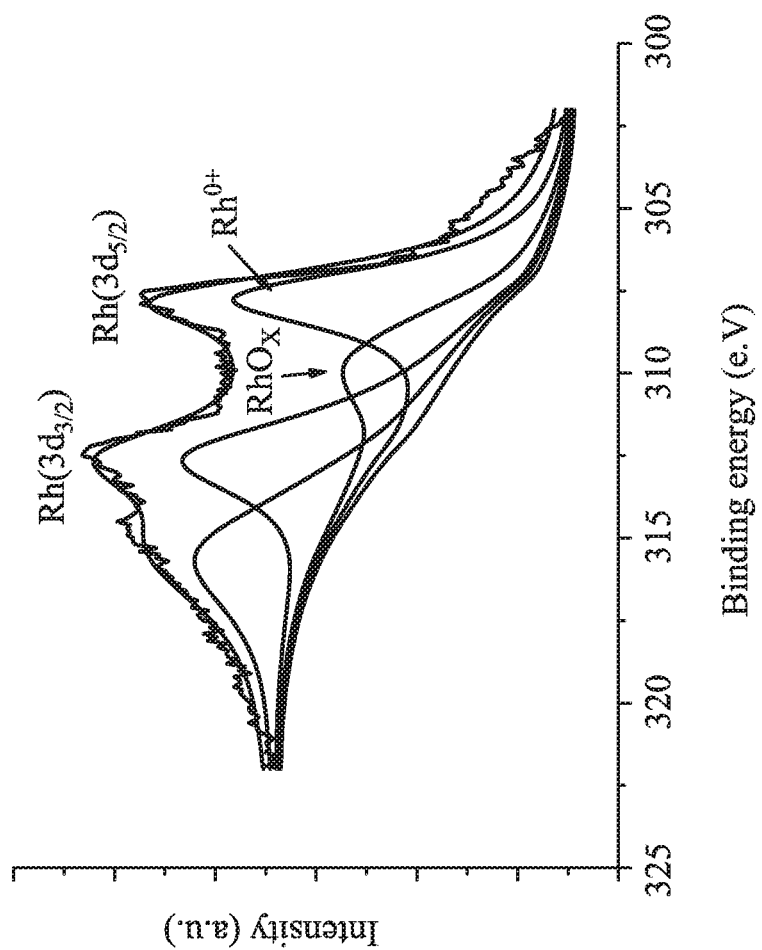
FIG. 11 is a graph showing measurement results of XPS peak fitting (Rh 3d) of the catalyst $Rh_{2.5}Pt_{2.5}$/carbon black of Embodiment 23.
Figure 12:
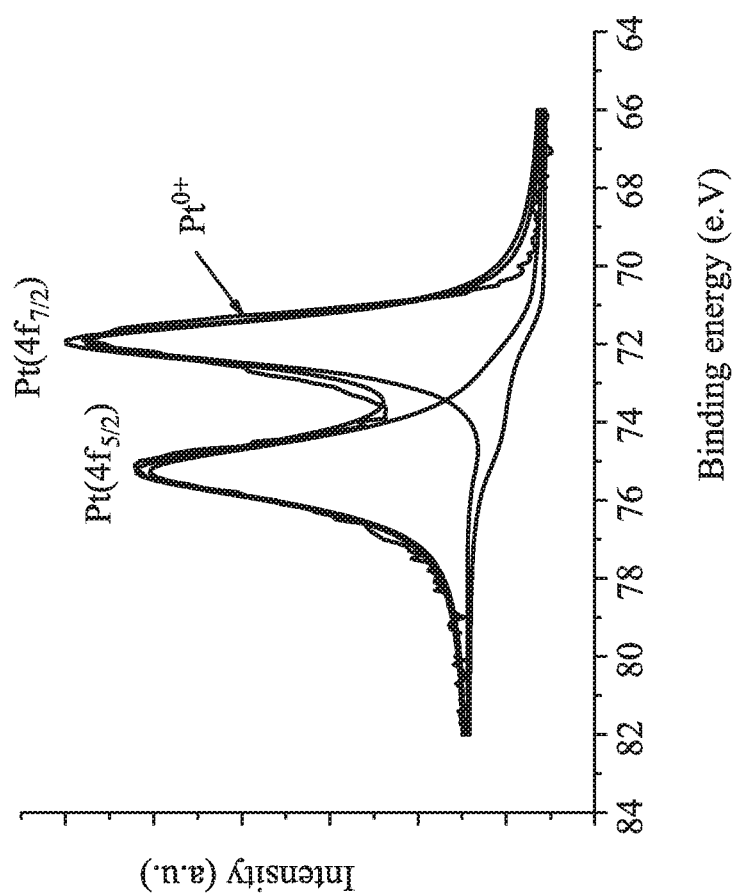
FIG. 12 is a graph showing measurement results of XPS peak fitting (Pt 4f) of the catalyst $Rh_{2.5}Pt_{2.5}$/carbon black of Embodiment 23.
Figure 13:
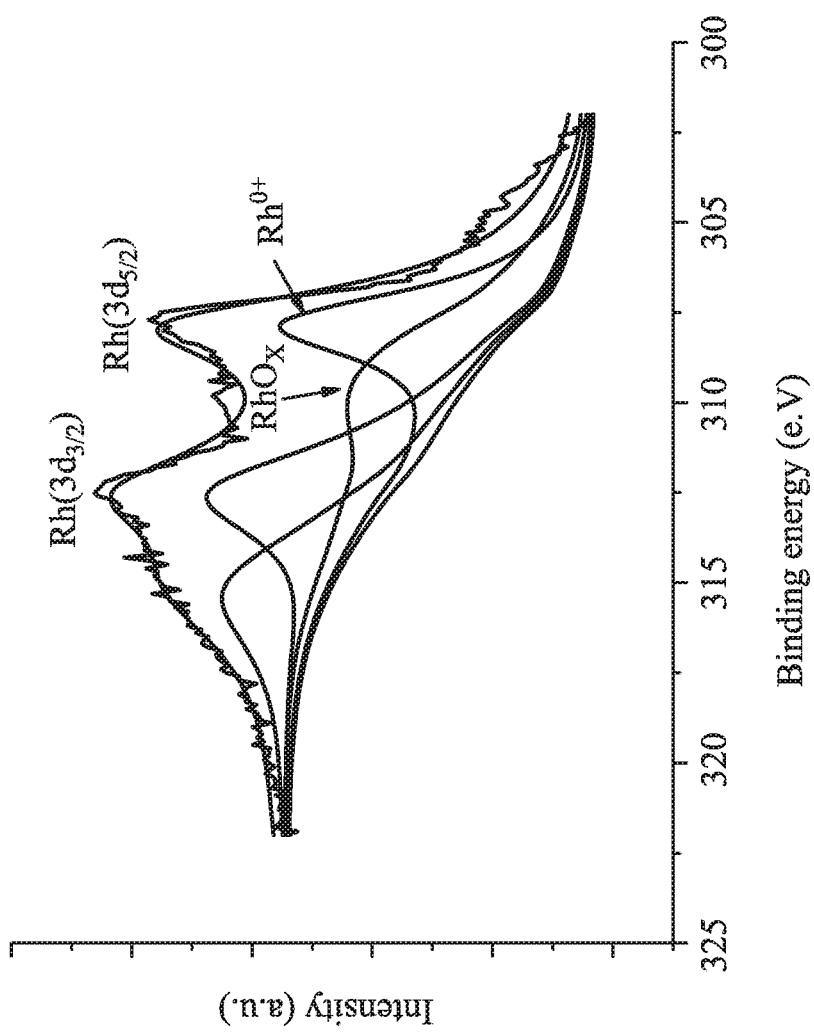
FIG. 13 is a graph showing measurement results of XPS peak fitting (Rh 3d) of the catalyst $Rh_{3.75}Pt_{1.25}$/carbon black of Embodiment 24.
Figure 14:
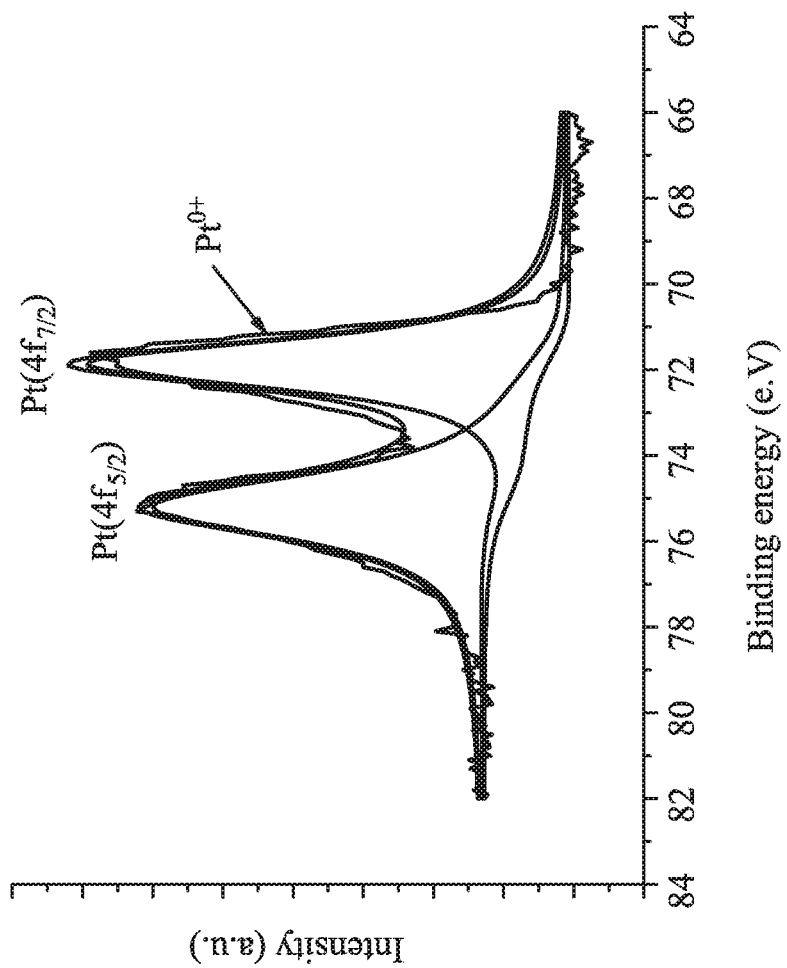
FIG. 14 is a graph showing measurement results of XPS peak fitting (Pt 4f) of the catalyst $Rh3.75Pt_{1.25}$/carbon black of Embodiment 24.

FIG. 5 to FIG. 14 are graphs showing measurement results of X-ray photoelectron spectroscopy (XPS) peak fitting of the commercial catalyst and the catalysts prepared in Examples 18-21, 23 and 24. FIG. 5 is graph showing measurement results of XPS peak fitting (Rh 3d) of the commercial catalyst $Rh_5$/C of Example 14. FIG. 6 is a graph showing measurement results of XPS peak fitting (Rh 3d) of the catalyst $Rh_5$/activated carbon of Example 18. FIG. 7 is a graph showing measurement results of XPS peak fitting (Rh 3d) of the catalyst $Rh_5$/mesoporous carbon of Example 19. FIG. 8 is a graph showing measurement results of XPS peak fitting (Rh 3d) of the catalyst $Rh_5$/carbon black of Example 20. FIG. 9 is a graph showing measurement results of XPS peak fitting (C 2s) of the catalyst $Rh_5$/carbon black of Example 20. FIG. 10 is a graph showing measurement results of XPS peak fitting (Rh 3d) of the catalyst $Rh_5$/carbon black-imp of Example 21. FIG. 11 is a graph showing measurement results of XPS peak fitting (Rh 3d) of the catalyst $Rh_{2.5}Pt_{2.5}$/carbon black of Example 23. FIG. 12 is a graph showing measurement results of XPS peak fitting (Pt 40 of the catalyst $Rh_{2.5}Pt_{2.5}$/carbon black of Example 23. FIG. 13 is a graph showing measurement results of XPS peak fitting (Rh 3d) of the catalyst $Rh_{3.75}Pt_{1.25}$/carbon black of Example 24. FIG. 14 is a graph showing measurement results of XPS peak fitting (Pt 4f) of the catalyst $Rh_{3.75}Pt_{1.25}$/carbon black of Example 24.

The relative atomic percentage (atom %) of the oxygen atoms in the catalyst, the atomic percentage of the rhodium converted to the oxidation state ($RhO_x$), the atomic percentage of the rhodium metal ($Rh^{0+}$), and the atomic ratio of the rhodium in the oxidation state to the rhodium metal $$\left(\frac{RhO_x}{Rh^0}\right)$$

could be calculated using the results of FIGS. 5-14. $RhO_x/Rh^{0+}$ was calculated by fitting the area under the line of $Rh(3d_{5/2})$, and the relative atomic percentage (atom %) of the oxygen atoms was estimated using the XPS full diagram. The above results are summarized in Table 3 below, and "BE" in Table 3 indicates binding energy.

The catalysts of Examples 14, 18-20, and 23-24 had at least 50 atom % of $RhO_x$, while the catalyst of Example 21 did not have $RhO_x$. This result confirmed that $RhO_x$ could not be produced by the wet impregnation method. The composition of the monometallic catalyst prepared by the modified microwave assisted polyol reduction method could be represented as $RhO_x$—Rh(0), and Rh of the rhodium oxide in the catalyst included two valence states, and the main valence state was $Rh^{+3}$, and the minor valence state was $Rh^{+1}$. In the bimetallic catalysts of Examples 23 and 24, the valence state of Pt metal in the bimetallic catalysts was $Pt^0$. The composition of the bimetallic catalyst can be represented as $RhO_x$—Rh(0)-Pt(0).

TABLE 3

XPS peak fitting calculation results of different catalysts

| Example | Catalyst | Relative atomic percentage of oxygen atoms (atom %) | $RhO_x$ (atom %) | $RhO_x$ BE (eV) | $Rh^{0+}$ (atom %) | $Rh^{0+}$ BE (eV) | $Pt^{+0}$ (atom %) | $Pt^{+0}$ BE (eV) | $\frac{RhO_x}{Rh^0}$ |
|---|---|---|---|---|---|---|---|---|---|
| 14 | $Rh_5$/C (commercial catalyst) | 14.0 | 49.2 | 309.0 | 50.8 | 307.5 | — | — | 0.97 |
| 18 | $Rh_5$/activated carbon | 14.6 | 54.6 | 309.0 | 45.4 | 307.6 | — | — | 1.20 |
| 19 | $Rh_5$/mesoporous carbon | 1.7 | 55.5 | 309.2 | 45.5 | 307.5 | — | — | 1.25 |
| 20 | $Rh_5$/carbon black | 4.6 | 53.9 | 309.3 | 46.1 | 307.6 | — | — | 1.04 |
| 21 | $Rh_5$/carbon black-imp | | ND | ND | 100 | 307.6 | — | — | 0 |
| 23 | $Rh_{2.5}Pt_{2.5}$/carbon black | | 59.5 | 309.6 | 40.5 | 307.7 | 100 | 71.9 | 0.68 |

TABLE 3-continued

XPS peak fitting calculation results of different catalysts

| Example | Catalyst | Relative atomic percentage of oxygen atoms (atom %) | $RhO_x$ (atom %) | $RhO_x$ BE (eV) | $Rh^{0+}$ (atom %) | $Rh^{0+}$ BE (eV) | $Pt^{+0}$ (atom %) | $Pt^{+0}$ BE (eV) | $\dfrac{RhO_x}{Rh^0}$ |
|---|---|---|---|---|---|---|---|---|---|
| 24 | $Rh_{3.75}Pt_{1.25}$/carbon black | 55.8 | 309.1 | 45.2 | 307.8 | 100 | 71.9 | 1.23 | |

Remarks: ND: not detected (D) Hydrogenation of BE 186 Using Monometallic Catalyst In the semi-batch system, the monometallic catalysts prepared by the methods according to the Examples described hereinbefore were used to hydrogenate BE186 using THF, EA or solvent G as the solvent. The hydrogenation reaction was carried out at 40° C. for 2 hours, and hydrogen gas was in a pressure of 1,000 psi. After the hydrogenation reaction was done, the product was analyzed. The detailed reaction conditions are listed in Table 4 below, in which the concentration (wt %) was calculated by (BE186 weight)/(BE186 weight+solvent weight).

TABLE 4

Hydrogenation of BE186 using monometallic catalyst

| Example | $W_{BE186}$ (g) | Catalyst type | $W_{catalyst}$ (g) | Solvent | $W_{solvent}$ (g) | Concentration (wt %) | Time (h) | Hydrogenation yield (%) | Specific activity ($h^{-1}$) |
|---|---|---|---|---|---|---|---|---|---|
| 25 | 2 | $Rh_5$/C(commercial catalyst) | 0.05 | THF | 2 | 50 | 2 | 59.6 | 64.2 |
| 26 | 2 | $Rh_5$/C(commercial catalyst) | 0.05 | EA | 2 | 50 | 2 | 65.7 | 70.8 |
| 27 | 2 | $Rh_5$/C(commercial catalyst) | 0.05 | Solvent G | 2 | 50 | 2 | 77.8 | 83.8 |
| 28 | 2 | $Rh_5$/activated carbon | 0.05 | THF | 2 | 50 | 2 | 46.5 | 50.1 |
| 29 | 2 | $Rh_5$/activated carbon | 0.05 | EA | 2 | 50 | 2 | 52.4 | 56.5 |
| 30 | 2 | $Rh_5$/activated carbon | 0.05 | Solvent G | 2 | 50 | 2 | 59.1 | 63.7 |
| 31 | 2 | $Rh_5$/mesoporous carbon | 0.05 | THF | 2 | 50 | 2 | 46.7 | 50.3 |
| 32 | 2 | $Rh_5$/mesoporous carbon | 0.05 | EA | 2 | 50 | 2 | 62.7 | 67.6 |
| 33 | 2 | $Rh_5$/mesoporous carbon | 0.05 | Solvent G | 2 | 50 | 2 | 72.6 | 78.2 |
| 34 | 2 | $Rh_5$/carbon black | 0.05 | THF | 2 | 50 | 2 | 75.3 | 81.1 |
| 35 | 2 | $Rh_5$/carbon black | 0.05 | EA | 2 | 50 | 2 | 98.8 | 106.5 |
| 36 | 2 | $Rh_5$/carbon black | 0.05 | Solvent G | 2 | 50 | 2 | 100 | 107.7 |
| 37 | 2 | $Rh_5$/carbon black-imp | 0.05 | Solvent G | 2 | 50 | 2 | 38.7 | 41.7 |
| 38 | 2 | $Rh_5$/carbon black-CFD | 0.05 | Solvent G | 2 | 50 | 2 | 28.6 | 30.8 |
| 39 | 2 | $Rh_8$/carbon black | 0.05 | THF | 2 | 50 | 2 | 100 | 67.3 |
| 40 | 2 | $Rh_8$/carbon black | 0.05 | EA | 2 | 50 | 2 | 100 | 67.3 |
| 41 | 2 | $Rh_8$/carbon black | 0.05 | Solvent G | 2 | 50 | 2 | 100 | 67.3 |

Remarks:
Catalyst type: represented in the form of $M_x$/carbon support, M = metal species, and X = the theoretical wt % loading of the metal
Carbon Black: Vulcan ® XC72
Solvent G: 3 wt % $H_2O$ and 97 wt % EA
$W_{BE186}$: BE186 weight
$W_{catalyst}$: catalyst weight
$W_{solvent}$: solvent weight In Examples 25-41 of Table 4, the hydrogenation yield using the commercial catalyst or the catalysts prepared by the modified microwave assisted polyol reduction method was higher than the hydrogenation yield that using the catalyst prepared by the wet impregnation method (Example 37) and the catalyst prepared using the CFD method (Example 38). These results proved that the reactivity of the catalyst was greatly increased when $RhO_x$ was contained in the catalyst, so that the catalyst had better hydrogenation reactivity.

According to the results of Table 4, under the same solvent condition, the hydrogenation yields that $Rh_5$/carbon black was used as the catalyst (Examples 34-36) were unexpectedly higher than the hydrogenation yields of the commercial catalyst $Rh_5$/C (Examples 25-27), catalyst $Rh_5$/activated carbon (Examples 28-30) and catalyst $Rh_5$/mesoporous carbon (Examples 31-33). Referring to the carbon support properties listed in Table 2, the carbon black had the smallest specific surface area and total pore volume. It was inferred that the catalyst ($Rh_5$/carbon black) of Examples 34-36 had better hydrogenation yield possibly because there was no obvious pore channel, so that bisphenol A epoxy resin was unable to stay in the pore channels for a long time period to proceed with side reactions during the hydrogenation reaction.

The oxygen atoms on the surface of the carbon black existed in various groups, for example, as shown in FIG. 9. Referring to the relative atomic percentage (atom %) of the oxygen atoms listed in Table 3, another reason why the catalyst of $Rh_5$/carbon black of Examples 34-36 had the better hydrogenation yields might be that the carbon black had an appropriate amount of oxygen-containing groups. Too less oxygen-containing groups would make the carbon support unable to anchor the metal particles and lead to leaching of the metal particles, affecting the hydrogenation reactivity, but excessive oxygen-containing groups would cause side reactions, such as ring-opening reactions of epoxy groups.

In Examples listed in Table 4, the solvent G had better hydrogenation yields for various catalysts. In addition, the hydrogenation yield of EA as the solvent was also higher than that of THF. These results were in agreement with the results of the foregoing Examples 1-13, confirming that EA and water or pure EA were preferred solvent choices for hydrogenation. Furthermore, EA and water are environmentally friendly green solvents relative to other highly toxic organic solvents.

In Examples 39-41 of Table 4, the benzene ring was able to be completely hydrogenated within 2 hours using the catalyst with a higher loading of active metal ($Rh_8$/carbon black) regardless of the hydrogenation reactions in any solvent. This result showed that increasing the active metal loading helped to increase the hydrogenation reactivity of the catalyst. In addition, it was also confirmed that the microwave polyol method could successfully prepare the catalyst having a high loading of active metal.

(E) Hydrogenation of BE186 Using Bimetallic Catalyst

In the semi-batch system, bimetallic catalysts prepared by the methods of Examples described hereinbefore were used to hydrogenate BE186. The hydrogenation reaction was carried out at 40° C. for 1 hour, and hydrogen gas was in a pressure of 1,000 psi. After the end of the hydrogenation reaction, the product was analyzed. The detailed reaction conditions are listed in Table 5 below, in which the concentration (wt %) was calculated by (BE186 weight)/(BE186 weight+solvent weight).

TABLE 5

Hydrogenation of BE186

| Example | $W_{BE186}$ (g) | Catalyst type | $W_{catalyst}$ (g) | Solvent | $W_{solvent}$ (g) | Concentration (wt %) | Time (h) | Hydrogenation yield (%) | Specific activity ($h^{-1}$) |
|---|---|---|---|---|---|---|---|---|---|
| 42 | 2 | $Rh_5$/carbon black | 0.05 | Solvent G | 2 | 50 | 1 | 66.9 | 144.2 |
| 43 | 2 | $Rh_{3.75}Pt_{1.25}$/carbon black | 0.05 | Solvent G | 2 | 50 | 1 | 77.9 | 190.4 |
| 44 | 2 | $Rh_{3.33}Pt_{1.67}$/carbon black | 0.05 | Solvent G | 2 | 50 | 1 | 69.8 | 178.6 |
| 45 | 2 | $Rh_{2.5}Pt_{2.5}$/carbon black | 0.05 | Solvent G | 2 | 50 | 1 | 89.5 | 252.5 |
| 46 | 2 | $Rh_{1.67}Pt_{3.33}$/carbon black | 0.05 | Solvent G | 2 | 50 | 1 | 65.3 | 205.4 |
| 47 | 2 | $Rh_{1.25}Pt_{3.75}$/carbon black | 0.05 | Solvent G | 2 | 50 | 1 | 62.4 | 208.3 |
| 48 | 2 | $Pt_5$/carbon black | 0.05 | Solvent G | 2 | 50 | 1 | 0 | 0 |

Remarks:
Catalyst type: represented in the form of $M_x$/carbon support, M is metal species, and x is the theoretical wt % of the metal loading
Carbon Black: Vulcan ® XC72
Solvent G: 3 wt % $H_2O$ and 97 wt % EA The catalyst of Example 45 ($Rh_{2.5}Pt_{2.5}$/carbon black) exhibited the highest hydrogenation yield (89.5%), followed by the catalyst of Example 43 ($Rh_{3.75}Pt_{1.25}$/carbon black) that the hydrogenation yield was 77.9%. The hydrogenation yield of the monometallic catalyst ($Rh_5$/carbon black) of Example 42 was 66.9%.

From Examples of Table 5 above, it was found that the weight ratio of Rh to Pt being 1:1 had the best hydrogenation ability when hydrogenating BE186. The specific activity of the catalyst of Example 45 was as high as 252.5 $h^{-1}$, which was higher than 144.2 $h^{-1}$ of Example 42 (monometallic catalyst $Rh_5$/carbon black). It was speculated that this phenomenon was a synergistic effect. Please note that the catalyst $Pt_5$/carbon black of Example 48 had no hydrogenation ability.

(F) Hydrogenation of BE503 Bisphenol A Epoxy Resin (DGEBA, Having a Molecular Weight of 1,500 g/mol, Supplied by Changchun Plastics Co., Ltd.)

The hydrogenation reaction of BE503 was carried out in the semi-batch system using the catalysts prepared by the methods according to Examples described hereinbefore. The hydrogenation reaction was performed at 40° C. for 2 hours, and hydrogen gas was in a pressure of 1,000 psi. The reaction conditions are listed in Table 6 below, in which the concentration (wt %) was $W_{BE503}/(W_{BE503}+W_{solvent})$. The structure of BE503 is as follows:

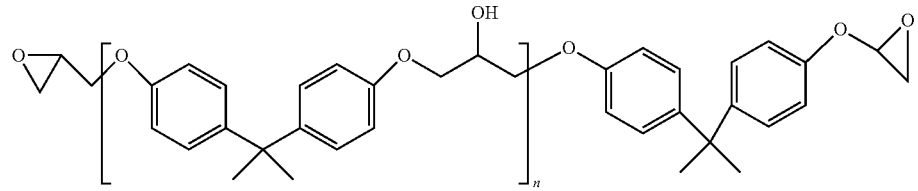

TABLE 6

Hydrogenation of BE503

| Example | $W_{BE503}$ (g) | Catalyst type | $W_{catalyst}$ (g) | Solvent | $W_{solvent}$ (g) | Concentration (wt %) | Time (h) | Hydrogenation yield (%) | Specific activity ($h^{-1}$) |
|---|---|---|---|---|---|---|---|---|---|
| 49 | 2 | $Rh_5$/carbon black | 0.05 | Solvent G | 4.66 | 30 | 2 | 50.6 | 12.3 |
| 50 | 2 | $Rh_{3.75}Pt_{1.25}$/carbon black | 0.05 | Solvent G | 4.66 | 30 | 2 | 65.6 | 18.0 |
| 51 | 2 | $Rh_{3.33}Pt_{1.67}$/carbon black | 0.05 | Solvent G | 4.66 | 30 | 2 | 61.2 | 17.6 |
| 52 | 2 | $Rh_{2.5}Pt_{2.5}$/carbon black | 0.05 | Solvent G | 4.66 | 30 | 2 | 87.8 | 27.8 |
| 53 | 2 | $Rh_{1.67}Pt_{3.33}$/carbon black | 0.05 | Solvent G | 4.66 | 30 | 2 | 56.7 | 20.0 |
| 54 | 2 | $Rh_{1.25}Pt_{3.75}$/carbon black | 0.05 | Solvent G | 4.66 | 30 | 2 | 58.7 | 22.0 |
| 55 | 2 | $Pt_5$/carbon black | 0.05 | Solvent G | 4.66 | 30 | 2 | 34.6 | 15.9 |
| 56 | 2 | $Rh_8$/carbon black | 0.05 | Solvent G | 4.66 | 30 | 2 | 64.1 | 9.7 |
| 57 | 2 | $Rh_4Pt_4$/carbon black | 0.05 | Solvent G | 4.66 | 30 | 2 | 100 | 19.8 |

Remarks:
Catalyst type: represented in the form of $M_x$/carbon support, M is metal species, and x is the theoretical wt % loading of the metal
Carbon Black: Vulcan® XC72
Solvent G: 3 wt % $H_2O$ and 97 wt % EA From Examples of Table 6, the hydrogenation yield of the bimetallic catalyst with a high metal loading ($Rh_4Pt_4$/carbon black) of Example 57 was as high as 100%. The hydrogenation yield of the bimetallic catalyst ($Rh_{2.5}Pt_{2.5}$/carbon black) of Example 52 was 87.8%. However, regarding the specific activity of the catalysts, the specific activity of the bimetallic catalyst ($Rh_{2.5}Pt_{2.5}$/carbon black) of Example 52 was 27.8 $h^{-1}$, which was higher than 19.8 $h^{-1}$ of the bimetallic catalyst with a high metal loading ($Rh_4Pt_4$/carbon black) of Example 57. Further, the specific activity of the bimetallic catalyst ($Rh_{2.5}Pt_{2.5}$/carbon black) of Example 52 was also higher than the specific activity of the monometallic catalysts ($Rh_5$/carbon black) and ($Rh_8$/carbon black) of Examples 49 and 56.

Compared with BE186 of Table 5, the specific activity of the same catalyst with respect to BE503 was considerably reduced, indicating that BE503 having a high molecular weight was much more difficult to be hydrogenated than BE186 having a low molecular weight.

In Examples of Table 7 shown below, the hydrogenation reactions of BE503 using various catalysts in three solvents were compared. Detailed reaction conditions are also summarized in Table 7.

In Examples listed in Table 7, the hydrogenation yields of the bimetallic catalyst $Rh_4Pt_4$/carbon black of Examples 71 and 72 in Solvent G or EA were 100%. Solvent G exhibited relatively higher hydrogenation yields for a variety of different catalysts. This result is consistent with the results of Examples in Table 4 above. It was again confirmed that the mixture of EA and water was the preferred solvent choice.

(G) Hydrogenation of BE507 Bisphenol A Epoxy Resin (DGEBA, Having a Molecular Weight of 3,550 g/mol, Supplied by Changchun Plastics Co., Ltd.)

The hydrogenation reaction of BE507 was carried out in the semi-batch system using the catalysts prepared by the methods according to Examples described hereinbefore. The hydrogenation reaction was performed at 40° C. for 2 hours, and hydrogen gas was in a pressure of 1,000 psi. The reaction conditions are listed in Table 8 below, in which the concentration (wt %) was $W_{BE507}/(W_{BE507}+W_{solvent})$. BE507 was similar in structure to BE503, with only different molecular weights.

TABLE 7

Hydrogenation of BE503

| Example | $W_{BE503}$ (g) | Catalyst type | $W_{catalyst}$ (g) | Solvent | $W_{solvent}$ (g) | Concentration (wt %) | Time (h) | Hydrogenation yield (%) | Specific activity ($h^{-1}$) |
|---|---|---|---|---|---|---|---|---|---|
| 58 | 2 | $Rh_5$/C(commercial catalyst) | 0.05 | THF | 4.66 | 30 | 2 | 30.2 | 7.3 |
| 59 | 2 | $Rh_5$/C(commercial catalyst) | 0.05 | EA | 4.66 | 30 | 2 | 34.8 | 8.4 |
| 60 | 2 | $Rh_5$/C(commercial catalyst) | 0.05 | Solvent G | 4.66 | 30 | 2 | 47.3 | 11.5 |
| 61 | 2 | $Rh_5$/carbon black | 0.05 | THF | 4.66 | 30 | 2 | 44.7 | 10.8 |
| 62 | 2 | $Rh_5$/carbon black | 0.05 | EA | 4.66 | 30 | 2 | 45.7 | 11.1 |
| 63 | 2 | $Rh_5$/carbon black | 0.05 | Solvent G | 4.66 | 30 | 2 | 50.6 | 12.3 |
| 64 | 2 | $Rh_{2.5}Pt_{2.5}$/carbon black | 0.05 | THF | 4.66 | 30 | 2 | 55.7 | 17.7 |
| 65 | 9 | $Rh_{2.5}Pt_{2.5}$/carbon black | 0.05 | EA | 4.66 | 30 | 2 | 74.0 | 23.5 |
| 66 | 2 | $Rh_{2.5}Pt_{2.5}$/carbon black | 0.05 | Solvent G | 4.66 | 30 | 2 | 87.8 | 27.8 |
| 67 | 2 | $Rh_8$/carbon black | 0.05 | THF | 4.66 | 30 | 2 | 64.1 | 9.7 |
| 68 | 2 | $Rh_8$/carbon black | 0.05 | EA | 4.66 | 30 | 2 | 65.3 | 9.9 |
| 69 | 2 | $Rh_8$/carbon black | 0.05 | Solvent G | 4.66 | 30 | 2 | 73.3 | 11.1 |
| 70 | 2 | $Rh_4Pt_4$/carbon black | 0.05 | THF | 4.66 | 30 | 2 | 93.8 | 18.6 |
| 71 | 2 | $Rh_4Pt_4$/carbon black | 0.05 | EA | 4.66 | 30 | 2 | 100 | 19.8 |
| 72 | 2 | $Rh_4Pt_4$/carbon black | 0.05 | Solvent G | 4.66 | 30 | 2 | 100 | 19.8 |

Remarks:
Catalyst type: represented in the form of $M_x$/carbon support, M is metal species, and x is the theoretical wt % loading of the metal
Carbon Black: Vulcan® XC72
Solvent G: 3 wt % $H_2O$ and 97 wt % EA

TABLE 8

Hydrogenation of BE507

| Example | $W_{BE186}$ (g) | Catalyst | $W_{catalyst}$ (g) | Solvent | $W_{solvent}$ (g) | Concentration (wt %) | Time (h) | Hydrogenation yield (%) | Specific activity ($h^{-1}$) |
|---|---|---|---|---|---|---|---|---|---|
| 73 | 2 | Rh$_5$/C (commercial catalyst) | 0.05 | Solvent G | 6.12 | 24.6 | 2 | 26.0 | 2.7 |
| 74 | 2 | Rh$_5$/carbon black | 0.05 | Solvent G | 6.12 | 24.6 | 2 | 42.7 | 4.5 |
| 75 | 2 | Rh$_{2.5}$Pt$_{2.5}$/carbon black | 0.05 | Solvent G | 6.12 | 24.6 | 2 | 88.7 | 12.3 |
| 76 | 2 | Rh$_8$/carbon black | 0.05 | Solvent G | 6.12 | 24.6 | 2 | 69.0 | 4.6 |
| 77 | 2 | Rh$_4$Pt$_4$/carbon black | 0.05 | Solvent G | 6.12 | 24.6 | 2 | 100 | 8.6 |

Remarks:
Catalyst type: represented in the form of M$_x$/carbon support, M is metal species, and x is the theoretical wt % loading of the metal
Carbon Black: Vulcan ® XC72
Solvent G: 3 wt % H$_2$O and 97 wt % EA From Examples of Table 8, the hydrogenation yield of the bimetallic catalyst with a high metal loading (Rh$_4$Pt$_4$/carbon black) of Example 77 was as high as 100%. The hydrogenation yield of the bimetallic catalyst (Rh$_{2.5}$Pt$_{2.5}$/carbon black) of Example 75 was 88.7%. However, regarding the specific activity of the catalyst, the specific activity of the bimetallic catalyst (Rh$_{2.5}$Pt$_{2.5}$/carbon black) of Example 75 was 12.3 h$^{-1}$, which was higher than 8.6 h$^{-1}$ of the bimetallic catalyst with a high metal loading (Rh$_4$Pt$_4$/carbon black) of Example 77. Further, the specific activity of the bimetallic catalyst (Rh$_{2.5}$Pt$_{2.5}$/carbon black) of Example 75 was also higher than the specific activity of the monometallic catalysts (Rh$_5$/carbon black) and (Rh$_8$/carbon black) of Examples 74 and 76.

Compared with BE503 of Table 7, the specific activity of the same catalyst with respect to BE507 was also considerably decreased, indicating that BE507 having a high molecular weight was much more difficult to be hydrogenated than BE503 having a relatively lower molecular weight.

(H) Ring-Opening Ratios of Epoxy Groups of Hydrogenation Reaction Products of BE186, BE503 and BE507

In the semi-batch system, BE186, BE503, and BE507 were hydrogenated by using the catalysts listed in Table 9, and the ratio of the epoxy ring opening of the products were analyzed. The hydrogenation reaction was carried out at 40° C. with 0.05 g of the catalysts, in which hydrogen gas was in a pressure of 1,000 psi. The detailed reaction conditions are listed in Table 9 below, in which the concentration (wt %) was $W_{epoxy}/(W_{epoxy}+W_{solvent})$.

TABLE 9

Ratios of epoxy ring opening of hydrogenation products of BE186, BE503 and BE507

| Example | Epoxy resin type | $W_{epoxy}$ (g) | Catalyst | $W_{catalyst}$ (g) | Solvent | Concentration (wt %) | Time (h) | Hydrogenation yield (%) | Ring-opening ratio (%) | Specific activity ($h^{-1}$) |
|---|---|---|---|---|---|---|---|---|---|---|
| 78 | BE186 | 2 | Rh$_5$/carbon black | 0.05 | Solvent G | 50 | 2 | 100 | 9.42 | 107.7 |
| 79 | BE186 | 2 | Rh$_{2.5}$Pt$_{2.5}$/carbon black | 0.05 | Solvent G | 50 | 1.5 | 96.3 | 29.06 | 181.2 |
| 80 | BE186 | 2 | Rh$_4$Pt$_4$/carbon black | 0.05 | Solvent G | 50 | 1 | 100 | 42.26 | 176.4 |
| 81 | BE503 | 2 | Rh$_{2.5}$Pt$_{2.5}$/carbon black | 0.05 | Solvent G | 30 | 3 | 99.2 | 81.36 | 20.9 |
| 82 | BE503 | 2 | Rh$_{2.5}$Pt$_{2.5}$/carbon black | 0.05 | Solvent G | 30 | 2 | 100 | 61.43 | 31.7 |
| 83 | BE503 | 2 | Rh$_4$Pt$_4$/carbon black | 0.05 | Solvent G | 30 | 2 | 100 | 59.62 | 19.8 |
| 84 | BE507 | 2 | Rh$_{2.5}$Pt$_{2.5}$/carbon black | 0.05 | Solvent G | 24.6 | 3 | 100 | 17.83 | 9.2 |
| 85 | BE507 | 2 | Rh$_{2.5}$Pt$_{2.5}$/carbon black | 0.05 | Solvent G | 24.6 | 5 | 100 | 72.58 | 5.5 |
| 86 | BE507 | 2 | Rh$_4$Pt$_4$/carbon black | 0.05 | Solvent G | 24.6 | 2 | 100 | 59.57 | 8.6 |

Remarks:
Example 82: performing at 60° C. and hydrogen gas in a pressure of 1,000 psi
Catalyst type: represented in the form of M$_x$/carbon support, M is metal species, and x is the theoretical wt % loading of the metal
Carbon Black: Vulcan ® XC72
Solvent G: 3 wt % H$_2$O and 97 wt % EA From the results of BE186 (Examples 78-80) of Table 9, it was observed that the monometallic catalyst (Rh$_5$/carbon black) exhibited a reaction rate lower than that of the bimetallic catalyst (Rh$_{2.5}$Pt$_{2.5}$/carbon black and Rh$_4$Pt$_4$/carbon black), but the monometallic catalyst (Rh$_5$/carbon black) possessed a lower ratio of epoxy ring opening. The bimetallic catalyst (Rh$_{2.5}$Pt$_{2.5}$/carbon black and Rh$_4$Pt$_4$/carbon black) exhibited a faster reaction rate, but its ring-opening ratio was significantly higher than that of the monometallic catalyst (Rh$_5$/carbon black). Therefore, it was inferred that Rh was the catalyst with high selectivity of benzene rings in hydrogenation, whereas Rh—Pt was the catalyst with high reactivity of benzene rings in hydrogenation.

(I) Optimization of Ring-Opening Ratio of Epoxy Groups of BE186

In a semi-batch system, the hydrogenation reactions of BE186 were carried out with the catalysts in experimental conditions listed in Table 10, and the ratios of epoxy ring opening of the products were analyzed.

TABLE 10

Optimization of ring-opening ratio of epoxy groups of BE186

| Example | $W_{BE186}$ (g) | Catalyst | $W_{catalyst}$ (g) | Solvent | $W_{catalyst}$ (g) | Temperature (° C.) | Viscosity (cps) | Time (h) | Hydrogenation yield (%) | Ring-opening ratio (%) | Specific activity (h$^{-1}$) |
|---|---|---|---|---|---|---|---|---|---|---|---|
| 87 | 2 | Rh$_5$/carbon black | 0.05 | EA | 2 | 40 | 3.71 | 2 | 98.8 | 3.1 | 106.5 |
| 88 | 2 | Rh$_5$/carbon black | 0.05 | Solvent G | 2 | 40 | 3.76 | 2 | 100 | 9.4 | 107.7 |
| 89 | 2 | Rh$_{2.5}$Pt$_{2.5}$/carbon black | 0.05 | EA | 2 | 40 | 3.71 | 1 | 74.9 | 12.2 | 211.3 |
| 90 | 5 | Rh$_5$/carbon black | 0.05 | Solvent G | 5 | 60 | 3.76 | 3 | 85.6 | 3.5 | 153.7 |
| 91 | 5 | Rh$_5$/carbon black | 0.05 | Solvent G | 5 | 60 | 3.76 | 3.5 | 100 | 3.4 | 153.9 |
| 92 | 5 | Rh$_5$/carbon black | 0.05 | EA | 5 | 60 | 3.71 | 4 | 100 | ND | 134.7 |
| 93 | 5 | Rh$_{2.5}$Pt$_{2.5}$carbon black | 0.05 | EA | 5 | 60 | 3.71 | 2 | 80.7 | 12.2 | 284.6 |

Remarks:
ND: indicates not detected
Catalyst type: represented in the form of M$_x$/carbon support, M is metal species, and x is the theoretical wt % loading of the metal
Carbon Black: Vulcan ® XC72
Solvent G: 3 wt % H$_2$O and 97 wt % EA In Example 87, the ring-opening ratio of the hydrogenation reaction using EA solvent without water was 3%. In Example 88, the ring-opening ratio of the hydrogenation reaction using the solvent G containing water was 9.4%, indicating that the solvent without water obtained a lower ratio of epoxy ring opening. Further, in Examples 90-93, the weight of BE186 was increased to 5 g (i.e., the weight ratio of the catalyst in the reaction system was decreased). In Example 90 and Example 91, the ring-opening ratio was controlled to a level of about 3% in the hydrogenation reaction, using solvent G containing water. In Example 92, EA was used as the solvent, and the ring-opening ratio was reduced to almost zero, and the hydrogenation yield was 100%. In Example 89 and Example 93, the bimetallic catalyst (Rh$_{2.5}$Pt$_{2.5}$/carbon black) was used, and its ring-opening ratios were higher than that of the monometallic catalyst (Rh$_5$/carbon black).

(J) Optimization of Ring-Opening Ratio of Epoxy Groups of BE503 and BE507

In a semi-batch system, hydrogenation reactions of BE503 were carried out with the bimetallic catalyst (Rh$_{2.5}$Pt$_{2.5}$/carbon black) in experimental conditions listed in Table 11, and ratios of epoxy ring opening of the products were analyzed. Further, hydrogenation reaction of BE507 was carried out in the experimental conditions listed in Table 12, and ring-opening ratios of epoxy groups of products were analyzed.

TABLE 11

Optimization of ring-opening ratio of epoxy groups of BE503

| Example | $W_{BE503}$ (g) | Catalyst | $W_{catalyst}$ (g) | Solvent | $W_{catalyst}$ (g) | Temperature (° C.) | viscosity (cps) | Time (h) | Hydrogenation yield (%) | Ring-opening ratio (%) | Specific activity (h$^{-1}$) |
|---|---|---|---|---|---|---|---|---|---|---|---|
| 94 | 5 | Rh$_{2.5}$Pt$_{2.5}$/carbon black | 0.05 | EA | 11.67 | 60 | 10.0 | 4 | 68.4 | 7.4 | 27.1 |
| 95 | 5 | Rh$_{2.5}$Pt$_{2.5}$/carbon black | 0.05 | Solvent G | 11.67 | 60 | 10.8 | 4 | 74.7 | 8.0 | 29.6 |
| 96 | 5 | Rh$_{2.5}$Pt$_{2.5}$/carbon black | 0.05 | Solvent G | 11.67 | 80 | 10.8 | 3 | 69.4 | 26.0 | 36.7 |
| 97 | 3.33 | Rh$_{2.5}$Pt$_{2.5}$/carbon black | 0.05 | Solvent G | 7.77 | 60 | 10.8 | 3 | 88.4 | 12.0 | 31.1 |
| 98 | 3.33 | Rh$_{2.5}$Pt$_{2.5}$/carbon black | 0.05 | Solvent G | 7.77 | 60 | 10.8 | 4 | 89.7 | 11.0 | 23.7 |
| 99 | 3 | Rh$_{2.5}$Pt$_{2.5}$/carbon black | 0.05 | Solvent G | 7 | 60 | 10.8 | 3 | 89.4 | 41.0 | 28.3 |
| 100 | 3 | Rh$_{2.5}$Pt$_{2.5}$/carbon black | 0.05 | Solvent G | 7 | 80 | 10.8 | 3 | 95.7 | 27.0 | 30.3 |
| 101 | 2 | Rh$_{2.5}$Pt$_{2.5}$/carbon black | 0.05 | Solvent G | 4.67 | 40 | 10.8 | 3 | 99.2 | 81.4 | 20.9 |
| 102 | 2 | Rh$_{2.5}$Pt$_{2.5}$/carbon black | 0.05 | Solvent G | 4.67 | 60 | 10.8 | 2 | 100 | 61.4 | 31.7 |

TABLE 12

Optimization of ring-opening ratio of epoxy groups of BE507

| Example | $W_{BE507}$ (g) | Catalyst | $W_{catalyst}$ (g) | Solvent | $W_{catalyst}$ (g) | Temperature (° C.) | viscosity (cps) | Time (h) | Hydrogenation yield (%) | Ring-opening ratio (%) | Specific activity (h$^{-1}$) |
|---|---|---|---|---|---|---|---|---|---|---|---|
| 103 | 2 | Rh$_{2.5}$Pt$_{2.5}$/carbon black | 0.05 | Solvent G | 6.13 | 40 | 13.0 | 3 | 100 | 17.6 | 9.2 |
| 104 | 3 | Rh$_{2.5}$Pt$_{2.5}$/carbon black | 0.05 | Solvent G | 9.2 | 60 | 13.0 | 3 | 92.3 | ND | 12.7 |

Remarks:
Catalyst type: represented in the form of M$_x$/carbon support, M = metal species, and X = the theoretical wt % loading of the metal
Carbon Black: Vulcan ® XC72
Solvent G: 3 wt % H$_2$O and 97 wt % EA
ND: not detected Referring to Examples 94 to 102 of Table 11, the hydrogenation yield and the ring-opening ratio were optimized by changing the weight of BE 503, the reaction temperature and the reaction time. As listed in Table 11, Examples 97 and 98 had relatively low ring-opening ratios of about 11 to 12% and maintained good hydrogenation yield.

Compared to Example 95, the reaction temperature was raised from 60° C. to 80° C. in Example 96, resulting in an increase in the ring-opening ratio. It was shown that an increase in temperature was advantageous for increasing the reaction rate. However, when the temperature was too high, the ring-opening ratio was also increased, so that there was a preferable temperature range. Similarly, the weight ratio of the epoxy resin to the catalyst was also an important parameter. If the ratio of the catalyst was too high, the ring-opening ratio increased (Examples 101 and 102). If the ratio of the catalyst was too low, the hydrogenation yield decreased. Therefore, there was a preferable range of the weight ratio.

In Example 104 of Table 12, the bimetallic catalyst ($Rh_{2.5}Pt_{2.5}$/carbon black) and the solvent G were used, and the hydrogenation yield was 92.3% and the ring-opening ratio was almost zero when the reaction temperature was 60° C.

Although the disclosure has been disclosed in the above Examples, those are not intended to limit the disclosure, and those may be altered or modified without departing from the spirit and scope of the disclosure. The scope of protection shall be subject to the definition of the scope of the present disclosure attached.

The invention claimed is:

1. A catalyst, comprising:
a carbon black support having a relative atomic percentage of oxygen atoms ranged from 2 atom % to 12 atom % on a surface of the carbon black support; and
a plurality of active metal particles distributed on the carbon black support, wherein each of the active metal particles comprises rhodium metal ($Rh^0$) and rhodium oxide.

2. The catalyst of claim 1, wherein the carbon black support has a specific surface area (BET) of less than 200 $m^2$/g.

3. The catalyst of claim 1, wherein the carbon black support has a pore volume of less than 0.5 $cm^3$/g.

4. The catalyst of claim 1, wherein each of the active metal particles further comprises platinum metal.

5. The catalyst of claim 1, wherein in the active metal particles, a number of rhodium atoms in the rhodium oxide is 45-60% of a total number of rhodium atoms.

6. The catalyst of claim 1, wherein the rhodium of the rhodium oxide comprises $Rh^{3+}$ and $Rh^{1+}$.

7. The catalyst of claim 1, wherein a ratio of a number of rhodium atoms of the rhodium oxide to a number of rhodium atoms of the rhodium metal ranges from 1 to 1.5.

8. A method for manufacturing a catalyst, comprising:
providing a reaction precursor comprising an alcohol reducing agent, a rhodium precursor, and a carbon black support;
mixing the reaction precursor with an alkali to obtain an alkaline precursor;
irradiating the alkaline precursor with microwaves to reduce the rhodium precursor in the alkaline precursor to an active metal containing rhodium metal and rhodium oxide; and
mixing the alkaline precursor irradiated by the microwaves with an acid such that the active metal containing the rhodium metal and the rhodium oxide is adsorbed on the carbon black support to form a catalyst.

9. The method of claim 8, wherein irradiating the alkaline precursor with the microwaves comprises: reducing 40-55 atom % of rhodium atoms in the rhodium precursor to the rhodium metal and reducing 45-60 atom % of rhodium atoms in the rhodium precursor to the rhodium oxide.

10. The method of claim 8, wherein the carbon black support has a pore volume of less than 0.5 $cm^3$/g.

11. The method of claim 8, wherein the carbon black support has a specific surface area of less than 200 $m^2$/g.

12. The method of claim 8, wherein the rhodium precursor comprises (i) rhodium chloride hydrate or (ii) rhodium chloride hydrate and chloroplatinic acid hexahydrate, wherein
mixing the reaction precursor with the alkali comprises:
forming an ion having a chemical formula of $Rh(OH)_6^{3-}$.

13. The method of claim 8, wherein mixing the reaction precursor with the alkali comprises: adjusting a pH value of the alkaline precursor to 10-13.

14. The method of claim 8, wherein mixing the alkaline precursor irradiated by the microwaves with the acid comprises: adjusting a pH value of the alkaline precursor to 1-4.

15. A method for hydrogenating an aromatic epoxy compound, comprising:
providing the catalyst of claim 1; and
hydrogenating a solution comprising an aromatic epoxy compound and a solvent using the catalyst, wherein the solvent comprises ethyl acetate.

16. The method of claim 15, wherein the solvent further comprises water, and a weight percentage of the water in the solvent ranges from 1 wt % to 5 wt %.

17. The method of claim 15, wherein in the hydrogenation reaction, a weight ratio of the aromatic epoxy compound to the catalyst is in a range of (2-5):0.05.

18. The method of claim 15, wherein the aromatic epoxy compound comprises at least one of bisphenol A epoxy resin and bisphenol A diglycidyl ether.

19. The method of claim 15, wherein the hydrogenating is performed in an environment at a temperature ranging from 30° C. to 80° C.

* * * * *